US007091018B2

(12) United States Patent
Fujiwara et al.

(10) Patent No.: US 7,091,018 B2
(45) Date of Patent: Aug. 15, 2006

(54) ENZYME GENE AND ITS EXPRESSION PRODUCT

(75) Inventors: Tsutomu Fujiwara, Tokushima (JP);
Takashi Okamoto, Hyogo (JP);
Masashi Niimi, Tokushima (JP);
Hiroyuki Kyushiki, Tokushima (JP);
Yasuchika Yamamoto, Tokushima (JP);
Atsunori Ueyama, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 224 days.

(21) Appl. No.: 10/297,599

(22) PCT Filed: Jun. 12, 2001

(86) PCT No.: PCT/JP01/04941

§ 371 (c)(1),
(2), (4) Date: Dec. 13, 2002

(87) PCT Pub. No.: WO01/96574

PCT Pub. Date: Dec. 20, 2001

(65) Prior Publication Data

US 2004/0132020 A1 Jul. 8, 2004

(30) Foreign Application Priority Data

Jun. 13, 2000 (JP) ............................. 2000-176631
Sep. 25, 2000 (JP) ............................. 2000-290679

(51) Int. Cl.
*C12N 9/10* (2006.01)
*C12N 1/12* (2006.01)
*C12N 15/00* (2006.01)
*C07H 21/04* (2006.01)

(52) U.S. Cl. .............................. 435/193; 435/4; 435/6; 435/69.1; 435/183; 435/252.3; 435/320.1; 536/23.2; 536/23.5; 530/350

(58) Field of Classification Search ................ 435/4, 435/6, 69.1, 183, 192, 193, 252.3, 320.1; 424/90.1; 530/350
See application file for complete search history.

(56) References Cited

FOREIGN PATENT DOCUMENTS

| EP | 824149 | 2/1998 |
|---|---|---|
| WO | 93/21330 | 10/1993 |
| WO | 2000/37617 | 6/2000 |

OTHER PUBLICATIONS

McKnight et al. GenBank Accession No. Q06210, 1994.*
G.L. McKnight et al.: "Molecular cloning, cDNA sequence, and bacterial expression of human glutamine: fructose-6-phosphate amidotransferase" J. Biol. Chem., vol. 267, No. 35, pp. 25208-25212 1992.

T. Oki et al.: "CDNA closing and mapping of a novel subtype of glutamine: ructose-6-phosphate amidotransferase (GFAT2) in human and mouse" GENOMICS, vol. 57, No. 2, pp. 227-234 1999.
Stephen Marshall et al.: "New insights into the metabolic regulation of insulin action and insulin resistance: role of glucose and amino acids" FASEB J., vol. 5, pp. 3031-3036 1991.
A. Giaccari et al.: "In vivo effects of glucosamine on insulin secretion and insulin sensitivity in the rat: Possible relevance to the maladaptive responses to chronic hyperglycaemia" DIABETOLOGIA, vol. 38, pp. 518-524 1995.
Stephen Marshall et al.: "Complete Inhibition of glucose-induced desensitization of the glucose transport system by inhibitors of mRNA synthesis" The Journal of Biological Chemistry, vol. 266, pp. 10155-10161 1991.
Stephen Marshall et al.: "Discovery of a metabolic pathway mediating glucose-induced desensitization of the glucose transport system" The Journal of Biological Chemistry, vol. 266, pp. 4706-4712 1991.
Andrew J. Paterson et al.: "Regulation of glutamine:fructose-6-phosphate amidotransferase gene transcription by epidermal growth factor and glucose" ENDOCRINOLOGY, vol. 136, pp. 2809-2816 1995.
Hannele Yki-Jarvinen et al.: "Increased glutamine:fructose-6-phosphate amidotransferase activity in skeletal muscle of patients with NIDDM" Diabetes, vol. 45, pp. 302-307 1996.
J. E. Dehaven, et al., Diabetes, vol. 50, No. 2, XP-009028613, pp. A284-A285, "A Novel Variant of Glutamine: Fructose-6-Phosphate Amidotransferase-1 (GFAT1) is Selectively Expressed in Skeletal Muscle", 2001.
M. Niimi, et al., J. Hum. Genet., vol. 46, No. 10, XP-002959859, pp. 566-571, "Identification of GFAT1-L, A Novel Splice Variant of Human Glutamine: Fructose-6-Phosphate Amidotransferase (GFAT1) That is Expressed Abundantly in Skeletal Muscle", 2001.
J. E. Dehaven, et al., Diabete, vol. 50, No. 11, XP-002959858, pp. 2419-2424, "A Novel Variant of Glutamine: Fructose-6-Phosphate Amidotransferase-1 (GFAT1) mRNA is Selectively Expressed in Striated Muscle", Nov. 2001.

(Continued)

*Primary Examiner*—Manjunath N. Rao
(74) *Attorney, Agent, or Firm*—Oblon, Spivak, McClelland, Maier & Neustadt, P.C.

(57) ABSTRACT

The present invention is drawn to a gene comprising a polynucleotide encoding a polypeptide composed of an amino acid sequence represented by SEQ ID NO: 1; a gene expression product produced through expression of the gene; a recombinant expression vector including the gene; a host cell (transformant) harboring the recombinant expression vector; a protein composed of an amino acid having an amino acid sequence represented by SEQ ID NO: 1; a therapeutic or preventive composition for hypoglycemia containing as an active ingredient the above-mentioned gene or protein; and an antibody capable of binding to the protein. Through use of the gene or an expression product thereof of the present invention, it is possible to elucidate the pathology of diabetes and develop drugs for treatment and prevention of diabetes via a new action mechanism.

8 Claims, 4 Drawing Sheets

OTHER PUBLICATIONS

G. L. McKnight, et al., DATABASE UNIPROT 'Online', AN Q06210; Q9BXF8, XP-002275456, 3 pages, Jun. 1, 1994.

P.P. Sayeski, et al., DATABASE UNIPROT 'Online', AN P47856; Q91XG9; Q99LP7; Q99MJ4, XP-002275457, 3 pages, Feb. 1, 1996.

G. L. McKnight, et al., DATABASE EMBL 'Online', AN M90516, XP-002275458, 3 pages, May 9, 1992.

G. L. McKnight, et al., DATABASE EMBL 'Online', AN AAQ51188, XP-002275459, 2 pages, May 20, 1994.

M. Coughenour, et al., DATABASE EMBL 'Online', AN AAA30882, XP002275460, 3 pages, Sep. 19, 2000, WO 2000/37617, Jun. 29, 2000.

NCI-CGAP (author), DATABASE EMBL 'Online', AN BE551543, XP-002275461, 2 pages, Aug. 11, 2000.

NCI-MGC (author), DATABASE EMBL 'Online', AN BG614693, XP-002275462, 2 pages, Apr. 24, 2001.

NCI-MGC (author), DATABASE EMBL 'Online', AN BG777268, XP-002275463, 2 pages, May 16, 2001.

* cited by examiner

ENZYME GENE AND ITS EXPRESSION PRODUCT

TECHNICAL FIELD

The present invention relates to a novel enzyme gene exhibiting an activity of glutamine:fructose-6-phosphate amidotransferase (hereinafter referred to as "GFAT"), and to a novel protein (enzyme) having an amino acid sequence encoded by the gene.

BACKGROUND ART

GFAT is an important enzyme catalyzing the conversion of fructose-6-phosphate into glucosamine-6-phosphate, which in a living organism is the rate-determining step in the hexosamine biosynthesis pathway. Recently, McKnight et al. have disclosed a human GFAT gene containing 681 amino acid residues (McKnight, G. L., et al., J. Biol. Chem., 267, 25208–25212 (1992)). Thereafter, Nishi et al. disclosed a novel human GFAT gene (U.S. Pat. No. 5,876,713).

Inhibitors of GFAT activity are thought to promote uptake of glucose into cells and to lower blood glucose level. Therefore, the inhibitors are expected to find use as drugs for treating diabetes. Uptake of glucose into cells is promoted by insulin, and the glucose in the cells is metabolized by the glycolytic pathway, whereby ATP is accumulated as an energy source. However, when uptake of glucose is excessive, fructose-6-phosphate, which is a glucose metabolite, enters the hexosamine biosynthesis pathway. Fructose-6-phosphate in the hexosamine biosynthetic pathway is converted into glucosamine-6-phosphate by the action of GFAT.

Metabolites of glucosamine-6-phosphate have been reported to prevent glucose transporters from transferring to cell membranes, resulting in suppression of uptake of glucose into cells (FASEB J., 5, 3031–3036 (1991); Diabetologia, 38, 518–524 (1995); J. Biol. Chem., 266, 10155–10161 (1991); J. Biol. Chem., 266, 4706–4712 (1991); and Endocrinology, 136, 2809–2816 (1995)).

Within the glucose metabolism pathway, the hexosamine biosynthetic pathway is considered to play a role as a feedback mechanism with respect to excessive uptake of glucose. In the hexosamine biosynthetic pathway, GFAT is important as a rate-determining enzyme. GFAT activity is known to be generally high in patients suffering non-insulin-dependent (type 2) diabetes mellitus, and GFAT activity is reported to be one of the causes of high blood glucose levels (Diabetes, 45, 302–307 (1996)).

In addition to human GFAT (J. Biol. Chem., 267, 25208–25212 (1992): U.S. Pat. No. 5,876,713), mouse GFAT, yeast GFAT, and *Escherichia coli* GFAT have been reported. These GFATs are highly homologous to human GFAT. However, at present, the presence of novel GFAT that is specific to skeletal muscle, which is an important tissue for glucose metabolism, is not known.

Isolation of a novel GFAT gene exhibiting GFAT activity enables elucidation of the regulatory function of GFAT in the hexosamine biosynthetic pathway. Isolation of a GFAT gene that is specifically expressed in a tissue such as skeletal muscle enables further elucidation of the glucose metabolism mechanism in the tissue. In addition, discovery of specific candidate compounds exhibiting an inhibition activity against a GFAT protein, the protein being an expression product having an amino acid sequence encoded by such a GFAT gene, could lead to development of a hypoglycemic drug having a novel action mechanism and contributing to prevention and treatment of diabetes.

In view of the foregoing, an object of the present invention is to isolate such a novel GFAT gene, particularly a GFAT gene which is specifically expressed in skeletal muscle.

DISCLOSURE OF THE INVENTION

In order to attain the aforementioned object, the present inventors have performed extensive studies, and have succeeded in cloning cDNA of a novel nucleotide sequence encoding a protein exhibiting a GFAT activity, from an cDNA library of human skeletal muscle. The present invention, which relates to desired protein and gene specifically expressed in human skeletal muscle and heart, has been accomplished on the basis of the successful cloning.

Accordingly, the present invention provides:

(1) a gene comprising the following polynucleotide (a), (b), (c), or (d)
   (a) a polynucleotide encoding a polypeptide composed of an amino acid sequence represented by SEQ ID NO: 2, or a complementary strand of the polynucleotide;
   (b) a polynucleotide having a homology of at least 98% to a polynucleotide encoding a polypeptide composed of an amino acid sequence represented by SEQ ID NO: 2, or a complementary strand of the polynucleotide;
   (c) a polynucleotide encoding a polypeptide composed of the amino acid sequence according to (a) in which one or more amino acids are deleted, substituted, or added, and having a GFAT activity, or a complementary strand of the polynucleotide; or
   (d) a polynucleotide encoding a polypeptide composed of an amino acid sequence having a homology of at least 98% to the amino acid sequence according to (a), or a complementary strand of the polynucleotide;
(2) a gene comprising the following polynucleotide (a) or (b):
   (a) a polynucleotide composed of a nucleotide sequence represented by SEQ ID NO: 1, or a complementary strand of the polynucleotide; or
   (b) a polynucleotide which is hybridized with a polynucleotide composed of the nucleotide sequence according to (a) under highly stringent conditions;
(3) a gene according to (2), which comprises a nucleotide sequence represented by SEQ ID NO: 1;
(4) a gene expression product produced through expression of a gene as recited in (1) or (2);
(5) a recombinant expression vector comprising a gene as recited in (1) or (2);
(6) a host cell harboring a recombinant expression vector as recited in (5);
(7) a transformant transformed by a recombinant expression vector as recited in (5);
(8) a protein represented by the following (a), (b), or (c):
   (a) a protein composed of an amino acid sequence represented by SEQ ID NO: 2;
   (b) a protein composed of the amino acid sequence according to (a) in which one or more amino acids are deleted, substituted, or added, and exhibiting a GFAT activity; or
   (c) a protein composed of an amino acid sequence having a homology of at least 98% to the amino acid sequence according to (a);
(9) a composition for treating or preventing hypoglycemia comprising, as an active ingredient, a gene as recited in (1) or (2) or a gene expression product as recited in (4);

(10) a composition for treating or preventing hypoglycemia comprising, as an active ingredient, a protein as recited in (8);

(11) an antibody, particularly a monoclonal antibody, which can be bound to any one selected from among a gene expression product as recited in (4), a protein as recited in (8), and fragments of the product and the protein;

(12) a screening method for a candidate compound which inhibits the enzyme activity of a gene as recited in (1), a gene expression product as recited in (4), or a protein as recited in (8), which method comprises: (i) reacting an antibody as recited in (11) with a test liquid containing a candidate compound, and with a protein as recited in (8) or a partial peptide of the protein, which has been labeled, in a competitive manner; and measuring the amount of the labeled protein or partial peptide which has bound to the antibody; (ii) reacting a test liquid containing a candidate compound with the aforementioned antibody and another labeled antibody simultaneously or consecutively, the antibodies being immobilized onto a carrier; and measuring the activity of a labeling agent on the carrier; or (iii) measuring the enzyme activity of a protein as recited in (8) or a partial peptide of the protein in the case in which the protein or the partial peptide is brought into contact with a substrate, and the enzyme activity of the protein or the partial peptide in the case in which the protein or the partial peptide is brought into contact with the substrate and a candidate compound, and comparing the enzyme activities from the respective cases; and

(13) a screening kit employed in a screening method as recited in (12), which comprises a buffer solution for measurement, a protein as recited in (8) or a partial peptide of the protein, and fructose-6-phosphate and glutamine serving as substrates.

The present invention also provides:

(14) a quantitative determination method for a protein composed of an amino acid sequence represented by SEQ ID NO: 2, (hereinafter the protein may be referred to as "GFAT1L protein") or a fragment of the protein in a test liquid, which method comprises: reacting, with a test liquid and with a labeled GFAT1L protein or a fragment of the protein, in a competitive manner, an antibody against a gene expression product of a gene containing a polynucleotide encoding a polypeptide composed of an amino acid sequence represented by SEQ ID NO: 2 or a gene containing a polynucleotide composed of a nucleotide sequence represented by SEQ ID NO: 1 (hereinafter each of these genes may be referred to as "GFAT1L gene"), or an antibody—against a GFAT1L protein or a fragment of the protein (i.e., partial peptide); and measuring the amount of the labeled GFAT1L protein or the fragment of the protein which binds to the antibody;

(15) a quantitative determination method for a protein of the present invention or a fragment of the protein in a test liquid, which method comprises: reacting a test liquid with the antibody as recited in (14) which is immobilized onto a carrier, and simultaneously or consecutively with an antibody against another labeled GFAT1L protein; and measuring the activity of a labeling agent on the carrier;

(16) a drug, particularly a drug for treating and preventing diabetes, which comprises an antibody against a GFAT1L protein (preferably an antibody against a GFAT1L protein exhibiting an activity for neutralizing the activity of the GFAT1L protein); and

(17) a screening method for a compound which inhibits GFAT enzyme activity, which method comprises measuring the enzyme activity of a GFAT1L protein or a fragment of the protein in the case in which the protein or the fragment is brought into contact with a substrate, and the enzyme activity of the protein or the fragment in the case in which the protein or the fragment is brought into contact with the substrate and a test compound, and comparing the enzyme activities exhibited in the respective cases.

The present invention also provides:

(18) an antisense DNA comprising a nucleotide sequence which is complementary to or substantially complementary to the DNA of a GFAT1L gene and exhibiting an action for inhibiting expression of the DNA;

(19) an antisense DNA of a GFAT1L gene comprising a nucleotide sequence which is substantially complementary to the DNA of a GFAT1L gene, wherein the entirety of the nucleotide sequence is complementary to the DNA or the nucleotide sequence has a homology of at least about 98% (preferably at least about 99%) to the nucleotide sequence complementary to the DNA; and

(20) a pharmaceutical composition, particularly a pharmaceutical composition for treating and preventing diabetes, which comprises an antisense DNA of a GFAT1L gene.

In the present specification, abbreviations of amino acids, peptides, nucleotide sequences, and nucleic acids are used according to the specification of IUPAC-IUB [IUPAC-IUB Communication on Biological Nomenclature, Eur. J. Biochem., 138: 9 (1984)], "Guideline for preparation of a specification containing a nucleotide sequence or an amino acid sequence" (the Japanese Patent Office ed.), and customary symbols employed in the art.

BEST MODE FOR CARRYING OUT THE INVENTION

Figure 1:
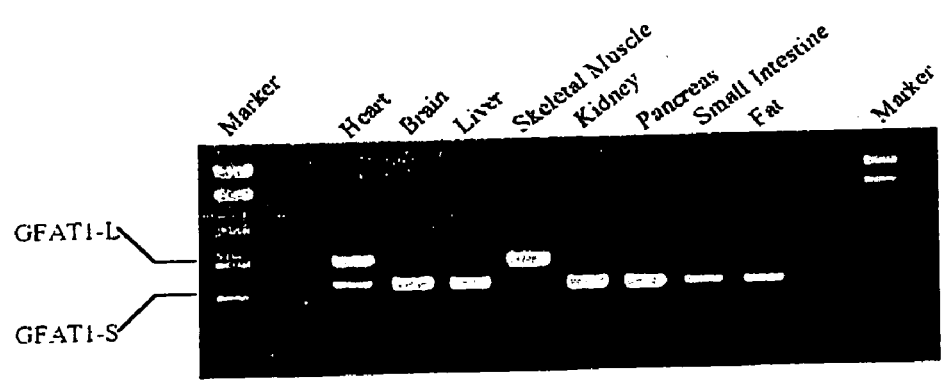
FIG. 1 is a photograph showing the expression patterns of the gene of the present invention exhibited in organs when products obtained through RT-PCR are subjected to agarose gel electrophoresis according to Example 2.

The gene and protein of the present invention will next be described in more detail.

A characteristic feature of the protein of the present invention resides in that the protein contains an amino acid sequence represented by SEQ ID NO: 2 or an amino acid sequence substantially identical to the amino acid sequence represented by SEQ ID NO: 2. For example, the protein of the present invention may be a protein derived from human cells, particularly human striated muscle cells, or from human tissue, particularly skeletal muscle or the heart. Alternatively, the protein of the present invention may be a synthetic protein.

Examples of the amino acid sequence substantially identical to the amino acid sequence represented by SEQ ID NO: 2 include an amino acid sequence having a homology of at least about 98%, preferably at least about 99%, to the amino acid sequence represented by SEQ ID NO: 2; and an amino acid sequence represented by SEQ ID NO: 2 in which one or more amino acids are deleted, substituted, or added. Examples of the protein composed of an amino acid sequence substantially identical to the amino acid sequence represented by SEQ ID NO: 2 include a protein composed of an amino acid sequence substantially identical to the amino acid sequence represented by SEQ ID NO: 2 and exhibiting a GFAT activity which is substantially qualitatively identical to that of the protein of the present invention composed of the amino acid sequence represented by SEQ ID NO: 2. Specific examples include gene products of homologues of the below-described GFAT1L gene (GFAT1L homologous genes including alleles), and proteins exhibiting identical GFAT activity of mammals such as human, horse, sheep, cattle, dog, monkey, cat, bear, rat, and rabbit.

As used herein, the term "substantially qualitatively identical" refers to the GFAT activities of proteins being characteristically (for example, physiologically, chemically, or pharmacologically) identical to each other. Therefore, quantitative parameters such as the degree of GFAT activity and molecular weight may differ from protein to protein.

GFAT activity may be measured by means of a known method; for example, the method by Marshall et al. (Marshall, et al., J. Biol. Chem., 266 (8), 4706–4712 (1991)).

As used herein, the term "GFAT activity" refers to the GFAT activity exhibited in the mixed inhibitory pattern when the GFAT activity is inhibited by UDP-N-acetylglucosamine by use fructose-6-phosphate as a substrate as shown in the below-described Examples. Therefore, the GFAT activity is clearly distinct from GFAT activity shown in the antagonistic inhibitory pattern. Hereinafter, the GFAT activity exhibiting the mixed inhibitory pattern specific to the present invention will be simply referred to as "GFAT activity."

The site of the aforementioned amino acid sequence at which amino acids are deleted, substituted, or added is arbitrary, so long as a protein containing the resultant modified amino acid sequence exhibits a GFAT activity. Similarly, the number of amino acids which are deleted, substituted, or added is arbitrary, so long as a protein composed of the resultant modified amino acid sequence exhibits a GFAT activity.

The gene of the present invention encodes a protein specific to the skeletal muscle and heart (GFAT1L protein) composed of the amino acid sequence represented by SEQ ID NO: 2 having 699 amino acid residues. Specific examples of the gene include a gene deduced from the DNA sequence of a PCR product called "GFAT1L" shown in the below-described Examples. The nucleotide sequence of the gene is represented by SEQ ID NO: 1, and contains 2097 nucleotides.

The GFAT1L gene of the present invention has been verified to have a novel nucleotide sequence, in which 54 nucleotides are inserted between the 684th nucleotide and 685th nucleotide of the GFAT gene cloned by McKnight et al. (McKnight, G. L., et al., J. Biol. Chem., 267, 25208–25212 (1992)).

Therefore, the amino acid sequence of the protein encoded by the gene of the present invention has an amino acid sequence in which 18 amino acids are inserted between the 228th amino acid and 229th amino acid of the amino acid sequence deduced from the gene reported by McKnight et al.

The protein of the present invention exhibits a GFAT activity, and is useful as, for example, a drug for ameliorating hypoglycemia. An antibody against the antisense DNA of the gene of the present invention or against an expression product of the gene is expected to exert an effect for treating diabetes, and the antibody can be utilized for screening a candidate compound serving as a drug for treating diabetes.

As used herein, the term "gene" encompasses double-stranded DNA and single-stranded DNA, such as a sense strand or an antisense strand constituting the double-stranded DNA. The length of the gene is not particularly limited. Therefore, unless otherwise specified, the gene (DNA) of the present invention encompasses double-stranded DNA containing human genome DNA, single-stranded DNA (sense strand) containing cDNA, single-stranded DNA (antisense strand) complementary to the sense strand, and fragments thereof.

The gene (DNA) of the present invention may contain a leader sequence, a coding region, an exon, and an intron. Examples of the polynucleotide include RNA and DNA. The DNA encompasses cDNA, genome DNA, and synthetic DNA. The polypeptide having a specific amino acid sequence encompasses fragments of the polypeptide, homologues of the polypeptide, derivatives of the polypeptide, and variants of the polypeptide.

Examples of the variants of the gene include naturally occurring allele variants, non-naturally occurring variants, and variants which have undergone deletion, substitution, addition, and insertion. The function of the polypeptide encoded by such a variant is not substantially changed.

The polypeptide encompasses a polypeptide having a homology of at least 98%, preferably 99%, to an allele, a homologue, or a naturally-occurring variant of the polypeptide.

The biological activity; i.e., GFAT activity, of the gene expression product of the present invention is, for example, an action for catalyzing the conversion of fructose-6-phosphate into glucosamine-6-phosphate. The GFAT activity is also an action for increasing the blood glucose level of human or mammals. Homology in relation to the DNA and the polypeptide may be analyzed through measurement by use of sequence analysis software employing a FASTA program (Clustal, V., Methods Mol. Biol., 25, 307–318 (1994)).

The variants of the gene of the present invention include a variant which causes silent or conservative substitution of amino acids; i.e., a varient characterized in that the amino acid residue encoded by the nucleotide sequence of the variant is not changed.

The types of conservatively substituted amino acid residues are described below.

| Original amino acid residue | Conservatively substituted amino acid residue |
|---|---|
| Ala | Ser |
| Arg | Lys |
| Asn | Gln, His |
| Asp | Glu |
| Cys | Ser |
| Gln | Asn |
| Glu | Asp |
| Gly | Pro |

| Original amino acid residue | Conservatively substituted amino acid residue |
|---|---|
| His | Asn or Gln |
| Ile | Leu or Val |
| Leu | Ile or Val |
| Lys | Arg or Glu |
| Met | Leu or Ile |
| Phe | Met, Leu, or Tyr |
| Ser | Thr |
| Thr | Ser |
| Trp | Tyr |
| Tyr | Trp or Phe |
| Val | Ile or Leu |

In general, one or more codons encoding a cysteine residue affect a disulfide bond of a specific polypeptide, and thus a cysteine residue is deleted, and the residue can be substituted by another amino acid residue.

As compared with the case in which an amino acid residue is conservatively substituted on the basis of the aforementioned list, when an amino acid residue is arbitrarily substituted, characteristics of the resultant protein are slightly changed.

The types of substitution generally expected to produce the greatest change in characteristics of a protein are as follow:

a) a hydrophilic amino acid residue such as seryl or threonyl is substituted by a hydrophobic amino acid residue such as leucyl, isoleucyl, phenylalanyl, valyl, or alanyl;

b) cysteinyl or prolyl is substituted by any of the other amino acid residues;

c) an amino acid residue having an electrically positive side chain, such as lysyl, arginyl, or histidyl, is substituted by an amino acid residue having an electrically negative side chain, such as glutamyl or aspartyl; and d) an amino acid residue having a very large side chain, such as phenylalanyl, is substituted by an amino acid residue having no side chain, such as glycyl.

The gene of the present invention and the gene product provide information and means very useful for elucidation, comprehension, diagnosis, prevention, and treatment of diabetes. The gene of the present invention is suitably employed for developing a novel drug for suppressing or inducing expression of the gene, the drug being utilized for the aforementioned treatment. Detection of expression of the gene product which suppresses or induces expression of the gene of the present invention in an individual or a tissue, or detection of mutation (deletion or point mutation) or abnormal expression of the gene, is suitably utilized for elucidation or diagnosis of diabetes.

The gene of the present invention encoding the aforementioned modified amino acid sequence may be used for detecting the gene of the present invention encoding the non-modified amino acid sequence.

Specific examples of the gene of the present invention include, but are not limited to, a GFAT1L gene having a nucleotide sequence encoding a protein composed of the amino acid sequence represented by SEQ ID NO: 2. The gene of the present invention also encompasses homologues of the GFAT1L gene.

As used herein, the term "homologues of the GFAT1L gene" refers to a series of related genes recognized as a gene family, the genes having sequence homology to the GFAT1L gene of the present invention (or the gene product), and having similarities to the GFAT1L gene in terms of the aforementioned structural characteristics, gene expression pattern, and the aforementioned biological function (for example, homology obtained by use of the FASTA program). Examples of the homologues of the GFAT1L gene include polynucleotides having a homology of at least 98%, preferably at least 99%, to a polynucleotide having a nucleotide sequence encoding a protein composed of the amino acid sequence represented by SEQ ID NO: 2, and polynucleotides complementary to the polynucleotides.

Modification (variation) of the aforementioned amino acid sequence may naturally occur through, for example, mutation or modification after translation. A naturally occurring gene (e.g., the GFAT1L gene of the present invention) may be modified artificially. The present invention encompasses all the modified genes having the aforementioned characteristics, regardless of causes or means f such modification and variation. The gene of the present invention encompasses alleles of the gene encoding a protein composed of the amino acid sequence represented by SEQ ID NO: 2.

Examples of the aforementioned artificial means include genetic engineering methods such as site-specific mutagenesis [Methods in Enzymology, 154, 350, 367–382 (1987); Methods in Enzymology; 100, 468 (1983); Nucleic Acids Res., 12, 9441 (1984); Zoku Seikagaku Jikken Koza 1 "Idenshi Kenkyu-ho II," Nippon Seikagakkai ed., p 105 (1986)]; chemical synthesis methods such as a phosphate triester method and a phosphate amidite method [J. Am. Chem. Soc., 89, 4801 (1967); J. Am. Chem. Soc., 91, 3350 (1969); Science, 150, 178 (1968); Tetrahedron Lett., 22, 1859 (1981); Tetrahedron Lett., 24, 245 (1983)]; and combinations of the above methods. More specifically, synthesis of DNA may be carried out through chemical synthesis by means of a phosphoramidite method or a triester method. Alternatively, synthesis of DNA may be carried out by use of a commercially available automatic oligonucleotide synthesis apparatus. Double-stranded DNA fragments may be produced from single-stranded products which are chemically synthesized by annealing synthesized complementary strands under appropriate conditions or by adding complementary strands by use of an appropriate primer sequence and DNA polymerase.

Specific embodiments of the gene of the present invention include a gene having a nucleotide sequence represented by SEQ ID NO: 1. The nucleotide sequence (coding region) shows an example of the combination of codons corresponding to individual amino acid residues of the amino acid sequence represented by SEQ ID NO: 2. The gene of the present invention is not limited to the gene having such a specific nucleotide sequence; the gene of the present invention may have a nucleotide sequence which is selected from the combinations of arbitrary codons corresponding to individual amino acid residues. Selection of codons may be carried out by means of a customary method. For example, selection of codons may be carried out in consideration of the frequency of use of codons of the host [Nucleic Acids Res., 9, 43 (1981)].

As described above, the gene of the present invention encompasses a gene composed of a nucleotide sequence having consistent homology to the nucleotide sequence represented by SEQ ID NO: 1.

The gene composed of a nucleotide sequence having consistent homology to the nucleotide sequence represented by SEQ ID NO: 1 refers to a polynucleotide composed of a nucleotide sequence having a homology of at least 98%, preferably at least 99%, to the nucleotide sequence represented by SEQ ID NO: 1, or a polynucleotide complementary to the polynucleotide.

Examples of the gene include a gene having a nucleotide sequence which is hybridized, under highly stringent conditions, with DNA having the nucleotide sequence represented by SEQ ID NO: 1; for example, in 0.2×SSC containing 0.1% SDS at 60° C. or in 0.1×SSC containing 0.1% SDS at 60° C.

The gene of the present invention can be easily produced or obtained by means of a customary genetic engineering method on the basis of sequence information in relation to specific examples of the gene disclosed herein [see Molecular Cloning 2d Ed, Cold Spring Harbor Lab. Press (1989); Zoku Seikagaku Jikken Koza "Idenshi Kenkyu-ho I, II, III," Nippon Seikagakkai ed. (1986)].

Specifically, a cDNA library is prepared, by means of a customary method, from an appropriate origin in which the gene of the present invention is expressed, and a desired clone is selected from the library by use of an appropriate probe or antibody specific to the gene of the present invention [e.g., Proc. Natl. Acad. Sci., USA., 78, 6613 (1981); Science, 222, 778 (1983)].

Examples of the aforementioned origin of cDNA include a variety of cells and tissues in which the gene of the present invention is expressed; and cultured cells derived from the cells or the tissues. Isolation of RNA or mRNA from such an origin, purification of mRNA, or obtaining and cloning of cDNA can be carried out by means of a customary method. In the present invention, a commercially available mRNA or cDNA library (e.g., product of Clontech Lab. Inc.) may be employed.

No particular limitation is imposed on the method for screening the gene of the present invention from a cDNA library, and the screening may be carried out by means of a customary method. Specific examples of the screening method include a method in which a cDNA clone corresponding to a protein produced on the basis of cDNA is chosen through immunological screening by use of an antibody specific to the protein; plaque hybridization by use of a probe which selectively binds to an intended DNA sequence; colony hybridization; and combinations thereof.

The probe employed for the screening may be DNA which is chemically synthesized on the basis of information in relation to the nucleotide sequence of the gene of the present invention, or may be the gene of the present invention which has been obtained or a fragment of the gene. Alternatively, the probe for the screening may be a sense primer or an antisense primer which is designed on the basis of information in relation to the nucleotide sequence of the gene of the present invention.

The nucleotide sequence used as the aforementioned probe is a partial nucleotide sequence corresponding to SEQ ID NO: 1, which has 15 or more continuous nucleotides, preferably 20 continuous nucleotides, more preferably 30 continuous nucleotides, much more preferably 50 continuous nucleotides, containing at least a portion of an insertion sequence site of 54 nucleotides. Alternatively, a positive clone having the aforementioned nucleotide sequence may be used as the probe.

The gene of the present invention is preferably obtained by means of a DNA/RNA amplification method employing PCR [Science, 230, 1350 (1985)]. When full-length cDNA is not easily obtained from a library, a RACE method [Rapid amplification of cDNA ends; Jikken Igaku, 12 (6), 35 (1994)], particularly, a 5'-RACE method [M. A. Frohman, et al., Proc. Natl. Acad. Sci., USA., 8, 8998 (1988)] is preferably employed.

A primer employed in such PCR is appropriately designed on the basis of sequence information of the GFAT1L gene elucidated by the present invention, and can be synthesized by means of a customary method. Isolation and purification of amplified DNA/RNA fragments can be carried out through a customary method as described above; for example, through gel electrophoresis.

The nucleotide sequence of the above-obtained gene of the present invention or DNA fragments can be determined by means of a customary method, such as a dideoxy method [Proc. Natl. Acad. Sci., USA., 74, 5463 (1977)] or a Maxam-Gilbert method [Methods in Enzymology, 65, 499 (1980)]. Alternatively, the nucleotide sequence can be conveniently determined by use of a commercially available sequencing kit.

When a portion or the entirety of the nucleotide sequence of the thus-obtained gene of the present invention is utilized, expression of the gene in individuals or various tissues can be detected specifically.

The detection of expression of the gene can be carried out by means of a customary method. Examples of the method for the detection include RNA amplification employing RT-PCR [Reverse transcribed-Polymerase chain reaction; E. S. Kawasaki, et al., Amplification of RNA. In PCR Protocol, A Guide to Methods and Applications, Academic Press, Inc., San Diego, 21–27 (1991)]; northern blotting analysis [Molecular Cloning, Cold Spring Harbor Lab. (1989)]; in situ RT-PCR [Nucl. Acids Res., 21, 3159–3166 (1993)]; measurement employing in situ hybridization on a cell-size scale; an NASBA method [Nucleic acid sequence-based amplification, Nature, 350, 91–92 (1991)]; and various other methods. Preferably, the detection is carried out by means of RT-PCR.

No particular limitation is imposed on the primer employed in PCR, so long as the primer can specifically amplify the gene of the present invention. The primer can be appropriately designed on the basis of the nucleotide sequence information of the gene of the present invention. Examples of the primer include a primer containing a partial nucleotide sequence of the gene of the present invention and having usually about 10 to 35 nucleotides, preferably about 15 to 30 nucleotides.

The gene of the present invention encompasses a DNA fragment used as a specific primer and/or a specific probe for detecting the gene.

The DNA fragment can be specified as DNA which is hybridized with DNA composed of the nucleotide sequence represented by SEQ ID NO: 1 under highly stringent conditions. The highly stringent conditions are not particularly limited, so long as the DNA fragment can be used as a primer or a probe. For example, the hybridization can be carried out under the condition as described above; i.e., in 0.2×SSC containing 0.1% SDS at 60° C., or in 0.1×SSC containing 0.1% SDS at 60° C.

By using the gene of the present invention, products of the gene (GFAT1L protein) or proteins containing the gene products can be easily and consistently mass-produced by means of a customary genetic engineering technique.

The present invention also provides a protein such as a GFAT1L protein encoded by the gene of the present invention; a vector containing the gene for producing the protein; a host cell transformed by the vector; and a production process for the protein by cultivating the host cell.

The protein of the present invention can be prepared on the basis of the nucleotide sequence information of the GFAT1L gene of the present invention by means of a customary gene-splicing technique [e.g., Science, 224, 1431 (1984); Biochem. Biophys. Res. Comm., 130, 692 (1985); Proc. Natl. Acad. Sci., USA., 80, 5990 (1983)].

More specifically, the protein is produced as follows: recombinant DNA (expression vector) which enables expression of a gene encoding the desired protein in a host cell is prepared; the DNA is introduced into the host cell to thereby transform the cell; the resultant transformant is cultivated; and the protein is recovered from the cultivated products.

A prokaryotic cell or a eukaryotic cell can be used as the aforementioned host cell. Examples of the prokaryotic host cell include widely used *Escherichia coli* and *Bacillus subtilis*. Preferably, *Escherichia coli* is used. Particularly preferably, *Escherichia coli* K-12 is used. Examples of the eukaryotic host cell include vertebrate cells and yeast cells. Preferred examples of the vertebrate cells include monkey COS cell [Cell, 23: 175 (1981)], Chinese hamster ovarian cell, and dihydrofolic-acid-reductase-defective cell strain of the ovarian cell [Proc. Natl. Acad. Sci., USA., 77: 4216 (1980)]. Preferred examples of the yeast cells include Saccharomyces cell. The host cell is not limited to the above examples.

When a prokaryotic cell is used as a host, a vector which can be replicated in the host cell is used. Examples of preferred vectors include an expression plasmid containing a promoter at an upstream position of the gene of the present invention, an SD (Shine-Dalgarno) sequence, and an initiation codon (e.g., ATG) necessary for initiation of protein synthesis, so that the gene can be expressed in the host cell. In general, an *Escherichia coli*-derived plasmid, such as pBR322, pBR325, pUC12, or pUC13, is widely used as the aforementioned vector. The vector is not limited to these examples, and a variety of known vectors may be used. Examples of commercially available *Escherichia coli*-derived vectors used for expression of the gene include pGEX-4T (product of Amersham Pharmacia Biotech); pMAL-C2 and pMAL-P2 (products of New England Biolabs); pET21 and pET21/lacq (products of Invitrogen); and pBAD/His (product of Invitrogen).

Examples of expression vectors used when a vertebrate cell is used as a host include a vector containing a promoter located at an upstream position of the gene of the present invention which is to be expressed, a splice site of RNA, a polyadenylation site, and a transcription termination sequence. If necessary, the vector may contain a replication origin. Specific examples of the expression vector include pSV2dhfr having an initial promoter of SV40 [Mol. Cell. Biol., 1: 854 (1981)]. In addition, a variety of commercially available known vectors can be used. Examples of commercially available vertebrate-cell-derived vectors used for expression of the gene include animal cell vectors, such as pEGFP-N and pEGFP-C (products of Clontech), pIND (product of Invitrogen), and pcDNA3.1/His (product of Invitrogen); and insect cell vectors, such as pFastBac HT (product of GibcoBRL), pAcGHLT (product of PharMingen), and pAc5/V5-His, pMT/V5-His, and pMT/Bip/V5-his (products of Invitrogen).

Specific examples of expression vectors used when a yeast cell is used as a host include pAM82 having a promoter corresponding to an acidic phosphatase gene [Proc. Natl. Acad. Sci., USA., 80: 1 (1983)]. Examples of commercially available yeast cell expression vectors include pPICZ (product of Invitrogen) and pPICZα (product of Invitrogen)

The type of a promoter employed is not particularly limited. For example, when *Escherichia* bacteria are used as a host, a tryptophan (trp) promoter, an lpp promoter, an lac promoter, an recA promoter, or a PL/PR promoter is preferably used. When *Bacillus* bacteria are used as a host, for example, an SP01 promoter, an SP02 promoter, or a penP promoter is preferably used. When yeast is used as a host, for example, a pH05 promoter, a PGK promoter, a GAP promoter, or an ADH promoter is preferably used. When an animal cell is used as a host, for example, an SV40-derived promoter, a retrovirus promoter, a metallothionein promoter, a heat shock promoter, a site megalovirus promoter, or an SRα promoter is preferably used.

A usual fused protein expression vector is preferably used as the expression vector of the gene of the present invention. Specific examples of the fused protein expression vector include pGEX (product of Promega) for expressing the gene as a fused protein with glutathione-S-transferase (GST).

Examples of the polynucleotide sequence which promotes expression and secretion of the polypeptide from a host cell include a secretion sequence and a leader sequence. When a bacterial host is used, for example, a marker sequence (hexahistidine tag) used for purification of a fused mature polypeptide is used. When a mammalian cell is used as a host, for example, a hemagglutinin (HA) tag is used.

No particular limitation is imposed on the method for introducing desired recombinant DNA (expression vector) into a host cell and transforming the host cell, and a variety of customary methods can be employed.

The thus-obtained transformant can be cultured by means of a customary method. Through cultured, the target protein of the present invention encoded by the desirably designed gene is expressed and produced (accumulated and secreted) inside or outside the cells of the transformant, or on the plasma membrane of the transformant.

In accordance with a host cell employed, the medium used for the culture may be selected from among a variety of conventionally used media. The culture may be carried out under conditions suitable for growth of the host cell.

If desired, the thus-obtained recombinant protein of the present invention may be subjected to separation and purification through a variety of separation techniques making use of physical and chemical properties of the protein [see "Biochemistry Data Book II," pp. 1175–1259, first edition, first printing, Jun. 23, 1980, published by Tokyo Kagaku Dojin; Biochemistry, 25 (25), 8274 (1986); Eur. J. Biochem., 163, 313 (1987)].

Specific examples of the separation technique include usual reconstruction treatment, treatment by use of a protein precipitant (salting-out), centrifugation, an osmotic pressure shock method, sonication, ultrafiltration, molecular sieve chromatography (gel filtration), adsorption chromatography, ion-exchange chromatography, affinity chromatography, high performance liquid chromatography (HPLC), dialysis, and combinations thereof. More preferably, affinity chromatography employing a column bound to an antibody specific to the protein of the present invention is carried out.

When a desired gene encoding the protein of the present invention is designed, the nucleotide sequence of the GFAT1L gene represented by SEQ ID NO: 1 is preferably utilized. If desired, the gene may be designed by appropriately selecting and modifying codons corresponding to the amino acid residues of the protein.

The protein of the present invention may be produced on the basis of the amino acid sequence represented by SEQ ID NO: 2 by means of a general chemical synthesis method. Examples of the synthesis method include a peptide synthesis method employing a usual liquid phase method or a solid phase method.

Specific examples of the peptide synthesis method include a stepwise elongation method in which amino acids are sequentially bound with one another on the basis of amino acid sequence information, to thereby elongate the chain of amino acids; and a fragment condensation method in which fragments composed of several amino acids are synthesized in advance, and the fragments are bound with one another through coupling reaction. The protein of the present invention may be synthesized by means of either of the methods.

In such peptide synthesis, condensation may be carried out by means of a customary method. Examples of the condensation method include an azide method, a mixed acid anhydride method, a DCC method, an active ester method, an oxidation-reduction method, a DPPA (diphenylphosphorylazide) method, a DCC+additive (1-hydroxybenzotriazole, N-hydroxysuccinamide, N-hydroxy-5-norbornane-2,3-dicarboxyimide) method, and a Woodward method.

A solvent employed in such a method can be appropriately selected from widely used solvents used for peptide condensation reaction. Examples of the solvent include dimethylformamide (DMF), dimethylsulfoxide (DMSO), hexaphophoroamide, dioxane, tetrahydrofuran (THF), ethyl acetate, and solvent mixtures thereof.

In the course of the aforementioned peptide synthesis, a carboxyl group of amino acid or peptide, which group is not involved in the reaction, may be protected typically through esterification, to thereby form esters such as lower alkyl esters; e.g., a methyl ester, an ethyl ester, a tert-butyl ester, and aralkyl esters; e.g., a benzyl ester, a p-methoxybenzyl ester, and a p-nitrobenzyl ester.

An amino acid having a functional group in its side chain; e.g., a hydroxyl group in a tyrosine residue, may be protected with a group such as an acetyl group, a benzyl group, a benzyloxycarbonyl group, or a tert-butyl group. However, the protection may optionally be performed. In addition, for example, a guanidino group in an arginine residue may be protected by an appropriate protective group such as a nitro group, a tosyl group, a p-methoxybenzenesulfonyl group, a methylene-2-sulfonyl group, a benzyloxycarbonyl group, an isobornyloxycarbonyl group, or an adamantyloxycarbonyl group.

Deprotection of these protective groups included in the aforementioned amino acids, peptides, and proteins of the present invention—final products—may be carried out through a routine method; e.g., catalytic reduction or use of a reagent such as liquid ammonia/sodium, hydrogen fluoride, hydrogen bromide, hydrogen chloride, trifluoroacetic acid, acetic acid, formic acid, or methanesulfonic acid.

The thus-obtained protein of the present invention may appropriately be purified through a variety of methods as described above. For example, there may be employed methods generally employed in the field of peptide chemistry; e.g., use of ion-exchange resin, partition chromatography, gel chromatography, and counter current distribution.

The protein of the present invention can be suitably used as an immunogen for producing its specific antibody. By use of the immunogen, a desired antiserum (polyclonal antibody) and monoclonal antibody can be produced.

The method itself of producing the antibody is well known to those skilled in the art. Thus, also in the present invention, the antibody can be produced through a routine method (see, for example, zoku-seikagaku jikken kouza "method for studying immunobiology," edited by The Japanese Biochemical Society (1986)).

The thus-obtained antibody can advantageously be used, for example, for purifying GFATL1 protein; assaying and identifying the protein through its immunological method. More specifically, since expression of the gene of the present invention is confirmed in the skeletal muscle tissue and the heart tissue, the antibody can be used for measuring the GFAT concentration in these tissues. In addition, a drug containing the antibody as an active ingredient is useful as a therapeutic or prophylactic agent against diseases such as diabetes and complications thereof.

The thus-obtained protein of the present invention is also useful, in the field of drugs, as a drug containing the protein as an active ingredient. Accordingly, the present invention provides a drug composition containing the protein of the present invention as an active ingredient.

As described above, the advantages, as a drug, of the protein of the present invention reside in promoting a GFAT activity of a polypeptide which is specific to the skeletal muscle recognized as an important tissue for glucose metabolism or promoting an action for mitigating hypoglycemia. These activities can be confirmed in accordance with a method; for example, a method described by Marshall et al. (*J. Biol. Chem.*, 266(8), 4706–4712 (1991)), which is described in the below-mentioned Examples in this specification.

In the above method, when glutamate formed by the action of GFAT is further reacted with glutamate dehydrogenase (GDH), APAD (coenzyme) is simultaneously reduced to APADH. The change in absorbance concomitant with reduction is measured, to thereby provide the GFAT activity. Specifically, in the method, an appropriately diluted soluble fraction (50 μl) of a GFAT1L *E. coli* solution is added to a substrate solution (40 mM sodium phosphate buffer, pH 7.5, 50 mM KCl, 1.25 mM EDTA, 0.3 mM APAD, 6 U/ml GDH, 0–6 mM glutamine, and 0–6 mM fructose-6-P (F6P)) (200 μl) placed in a 96-well microplate; the mixture is allowed to react at 37° C. for 60 minutes; and the change in absorbance due to the reaction is measured at 365 nm through spectrophotometry by use of a microplate reader.

The protein of the present invention serving as an active ingredient in a drug composition also encompasses pharmaceutically acceptable salts thereof. These salts are prepared through a method known in the art. Examples of the salts includes salts of an alkali metal such as sodium, potassium, or lithium; salts of an alkaline earth metal such as calcium, magnesium, or barium; and ammonium salts. The aforementioned salts further include acid-added salts produced through reaction of the protein of the present invention with an appropriate organic or inorganic acid. Examples of typical acid-added salts include, hydrochlorides, hydrobromides, sulfates, bisulfates, acetates, oxalates, valerates, oleates, laurates, borates, benzoates, lactates, phosphates, p-toluenesulfonates (tosylates), citrates, maleates, fumarates, succinates, tartrates, sulfonates, glycollates, maleates, ascorbates, benzenesulfonates, and naphthylates.

The aforementioned drug composition contains, as an active ingredient, the protein of the present invention in a pharmaceutically effective amount and, in combination, an appropriate drug carrier or a diluent.

Examples of the drug carrier which can be used in the aforementioned drug composition (drug preparation) include typically employed diluents and vehicles, in accordance with the form of use of the preparation. Specific examples include a filler, a bulking agent, a binder, a moisturizer, a disintegrant, a surfactant, and a lubricant, and the carrier is appropriately selected and used in accordance with the form of unit administration of the preparation to be produced.

Particularly preferably, the drug preparation of the present invention is prepared by appropriately using a variety of ingredients which are used in typical protein preparations and the like such as a stabilizer, a sterilizer, a buffer, a tonicity agent, a chelating agent, a pH-adjusting agent, and a surfactant.

Examples of the stabilizer include human serum albumin, typical L-amino acids, saccharides, and cellulose derivatives. These stabilizer can be used singly or in combination and can also be used in combination with another ingredient such as a surfactant. Possibly, such combination further enhances the stability of the active ingredient.

The aforementioned L-amino acids are not particularly limited, and any L-amino acid such as glycine, cysteine, or glutamic acid may be used.

No particular limitation is imposed on the aforementioned saccharides, and there may be used monosaccharides such as glucose, mannose, galactose, and fructose; sugar alcohols such as mannitol, inositol, and xylitol; disaccharides such as sucrose, maltose, and lactose; and polysaccharides such as dextran, hydroxypropyl starch, chondroitin sulfate, and hyaluronic acid; and derivatives thereof.

The surfactants are not particularly limited, and either ionic or nonionic surfactants may be used. Examples include polyoxyethylene glycol sorbitan alkyl esters, polyoxyethylene alkyl ethers, sorbitan monoacyl esters, and fatty acid glycerides.

The cellulose derivatives are not particularly limited, and cellulose derivatives such as methyl cellulose, ethyl cellulose, hydroxyethyl cellulose, hydroxypropyl cellulose, hydroxypropyl methyl cellulose, and sodium carboxymethyl cellulose may be used.

The aforementioned saccharides are added appropriately in a total amount of approximately 0.0001 mg or more per microgram of the active ingredient, preferably approximately 0.01–10 mg. The aforementioned surfactants are added appropriately in a total amount of approximately 0.00001 mg or more per microgram of the active ingredient, preferably approximately 0.0001–0.01 mg. Human serum albumin is added appropriately in an amount of approximately 0.0001 mg or more per microgram of the active ingredient, preferably approximately 0.001–0.1 mg. The amino-acid is added appropriately in an amount of approximately 0.001–10 mg per microgram of an active ingredient. The cellulose derivatives are added appropriately in a total amount of approximately 0.00001 mg or more per microgram of the active ingredient, preferably approximately 0.001–0.1 mg.

The amount of the active ingredient to be incorporated into the drug preparation of the present invention can appropriately be determined from a wide range and is appropriately controlled typically to approximately 0.00001–70 wt. %, preferably approximately 0.0001–5 wt. %.

The drug preparation of the present invention may contain a variety of additives such as a buffer, a tonicity agent, and a chelating agent. Examples of the buffer include boric acid, phosphoric acid, acetic acid, citric acid, $\epsilon$-aminocaproic acid, glutamic acid, and/or salts thereof (e.g., salts of an alkali metal such as sodium or potassium and salts of an alkaline earth metal such as calcium or magnesium). Examples of the tonicity agent include sodium chloride, potassium chloride, saccharides, and glycerin. Examples of the chelating agent include sodium edetate and citric acid.

The drug preparation of the present invention can be used in the solution preparation form. Alternatively, the preparation can also be used in a manner in which the preparation is lyophilized to assume a storable form and, thereafter, is dissolved in water, a buffer containing physiological saline, etc., to thereby form a preparation of appropriate concentration at the time of use.

The form of the administration unit of the drug preparation of the present invention can be determined from a variety of forms in accordance with the therapeutic purpose. Examples of typical administration forms include solids such as tablets, pills, powders, powdered drugs, granules, and encapsulated drugs; and liquids such as solutions, suspensions, emulsions, syrups, and elixirs. These administration forms are further divided, in accordance with the route of administration, into forms such as peroral drugs, parenteral drugs, nasotracheal drugs, transvaginal drugs, suppositories, sublingual drugs, and ointments. These forms can be mixed, shaped, and prepared in accordance with corresponding typical manners.

For example, when the preparation is formed into tablets, a variety of preparation carriers can be used. Examples include vehicles such as lactose, sucrose, sodium chloride, glucose, urea, starch, calcium carbonate, kaolin, crystalline cellulose, silicic acid, and potassium phosphate; binders such as water, ethanol, propanol, simple syrup, glucose solution, starch solution, gelatin solution, carboxymethyl cellulose, hydroxypropyl cellulose, methyl cellulose, and polyvinylpyrrolidone; disintegrants such as sodium carboxymethyl cellulose, carboxymethylcellulose-Ca, low-substitution-degree hydroxypropyl cellulose, dry starch, sodium alginate, powdered agar, powdered laminaran, sodium hydrogencarbonate, and calcium carbonate; surfactants such as polyoxyethylene sorbitan fatty acid esters, sodium lauryl sulfate, and stearic acid monoglyceride; disintegration-preventing agents such as sucrose, stearin, cacao butter, and hydrogenated oil; absorption-promoting agents such as quaternary ammonium bases, and sodium lauryl sulfate; humectants such as glycerol and starch; adsorbents such as starch, lactose, kaolin, bentonite, and colloidal silicic acid; and lubricants such as purified talc, stearate salts, powdered boric acid, and polyethylene glycol.

In addition, the tablets may optionally be coated with conventional coating material, to thereby form coated tablets. Examples of such tablets include sugar-coated tablets, gelatin-coated tablets, enteric-coated tablets, and film-coated tablets. Alternatively, the tablets may be formed into dual-layered tablets or multi-layered tablets.

When the preparations are formed into pills, there may be used preparation carriers which include vehicles such as glucose, lactose, starch, cacao butter, hydrogenated vegetable oils, kaolin, and talc; binders such as powdered acacia gum, powdered traganth, gelatin, and ethanol; and disintegrants such as laminaran and agar.

The encapsulated drugs are prepared, through a routine method, by mixing the active ingredient of the present invention and the preparation carriers as exemplified above, to thereby form a drug encapsulated with material such as hard gelatin or soft material.

The liquid preparations for peroral administration encompass pharmaceutically acceptable solutions, emulsions, suspensions, syrups, and elixirs, and they contain a generally employed inactive diluent such as water. The liquid preparations may further contain an adjuvant such as a humectant, an emulsifying agent, and a suspending agent. These preparations are prepared through routine methods.

When the drug preparations are formed into liquid preparations for parenteral administration; e.g., sterilized aqueous or non-aqueous solutions, emulsions, and suspensions, there can be used a diluent such as water, ethyl alcohol, propylene glycol, polyethylene glycol, ethoxylated isostearyl alcohol, polyoxygenated isostearyl alcohol, a polyoxyethylene sorbitan fatty acid ester, or a vegetable oil such as olive oil. In addition, organic esters which can be injected, such as ethyl oleate, may be incorporated. These liquid preparations may further contain a typical dissolution adjuvant such as a buffer, a humectant, an emulsifying agent, a suspending agent, a preservative, and a dispersant.

Sterilization can be performed through a method such as filtration by passing through a bacteria-holding filter; addition of a sterilizer; irradiation; or heating. Furthermore, the liquid preparation can also be prepared in the form of a sterilized solid composition which can be dissolved, immediately before use, in sterilized water or an appropriate sterilizable medium.

When the preparations are formed into suppositories and drugs for transvaginal administration, preparation carriers such as polyethylene glycol, cacao butter, higher alcohol, higher alcohol esters, gelatin, and semi-synthesized glycerides can be used.

When the preparations are formed into ointments such as paste, cream, and gel, diluents such as white petrolatum, paraffin, glycerin, cellulose derivatives, propylene glycol, polyethylene glycol, silicone, bentonite, and vegetable oil such as olive oil can be used.

Drug compositions for nasotracheal or sublingual administration can be prepared though a routine method by use of a known standard vehicle.

The drug of the present invention may contain additional components such as a colorant, a preservative, a perfume, a flavoring agent, a sweetening agent, and other pharmaceuticals.

No particular limitation is imposed on the method for administering the aforementioned drug preparations, and the method is determined in accordance with conditions such as the form of preparations, the status of patients; e.g., age or sex, and the gravity of disease. Specifically, tablets, pills, liquids, suspensions, emulsions, granules, and encapsulated drugs are administered perorally. The injections are intravenously administered singly or in combination with a typical replenisher such as glucose or amino acid, and if necessary, are administered intramuscularly, intracutaneously, subcutaneously, or intraperitoneally. The suppositories are administered intrarectally. The transvaginal drugs are administered transvaginally. The nasotracheal drugs are administered nasotracheally. The sublingual drugs are administered orally. The ointments are administered percutaneously.

The amount of the active ingredient to be contained in the aforementioned drug preparation and the dose of administration are not particularly limited. These amounts are appropriately selected from a wide range in accordance with conditions such as the desired therapeutic effect, the method of administration, the period of a therapy, and the status of patients such as age or sex. In general, the daily dose of administration is typically approximately 0.01 µg to 10 mg per kg of human body weight, preferably approximately 0.1 µg to 1 mg. The preparation may be administered at a single dose per day or in a divided manner.

The thus-obtained skeletal muscle-specific polypeptide of the present invention—the protein of the present invention—exhibits a GFAT activity, and the entirety or a portion of the protein per se is useful as a hypoglycemia-mitigating agent.

As shown in the below-described Examples, expression of the gene of the present invention is confirmed in the skeletal muscle tissue or the heart tissue. Thus, expression of the GFAT1L gene can intentionally be inhibited by producing an arbitrary gene expression vector including the entirety or a portion of the antisense DNA of the GFAT1L gene of the present invention and generating, by use of the vector, RNA having a sequence complementary to mRNA in cells of the skeletal muscle tissue so as to inhibit translation. Thus, the GFAT activity in the hexosamine biosynthesis pathway in the skeletal tissue can be inhibited, and uptake of glucose into cells is promoted, to thereby reduce the blood glucose level. As a result, glucose metabolism can be improved and the development of diabetes can be suppressed or mitigated. The gene of the present invention can possibly be employed as a gene therapy composition exhibiting an anti-diabetes action or as a gene-therapeutic agent exhibiting the same.

The present invention also provides a vector for use in gene therapy including the entirety or a portion of the GFAT1L gene and a drug containing, as an active ingredient, a cell into which the GFAT1L gene is introduced by use of the vector.

Accordingly, the present invention provides an introduction vector for use in gene therapy including a GFAT1L antisense gene containing the entirety or a portion of antisense DNA sequence represented by SEQ ID NO: 1; a cell into which the GFAT1L antisense gene is introduced by use of the vector; and a gene-therapeutic agent containing as active ingredients the introduction vector for use in gene therapy and a cell into which the GFAT1L antisense gene is introduced by use of the vector.

The present invention can also provide a diabetes therapeutic agent, characterized in that an introduction vector for use in gene therapy including a GFAT1L antisense gene containing the entirety or a portion of antisense DNA sequence represented by SEQ ID NO: 1 and a cell into which the GFAT1L antisense gene in introduced by use of the vector are administered to skeletal muscle cells or muscle tissue sites of a diabetes patient, to thereby improve glucose metabolism of these tissues and suppress the development of diabetes or improve glucose metabolism of a diabetes patient.

Furthermore, the present invention provides a drug containing as an active ingredient a virus introduction vector for gene therapy containing the aforementioned GAFT1L antisense gene, particularly such a drug for use in, for example, treatment to improve glucose metabolism in the skeletal muscle.

The gene therapy according to the present invention will next be described. Unless otherwise specified, customary methods of chemistry, molecular biology, microbiology, recombinant DNA techniques, genetics, and immunology can be employed so as to carry out the gene therapy described hereunder. Examples of these methods are described in Maniatis, T., et al., Molecular cloning: A laboratory manual (Cold Spring Harbor Laboratory, Cold Spring Harbor, N.Y. (1982)); Sambrook, J., et al., Molecular cloning: A laboratory manual, 2nd Ed. (Cold Spring Harbor Laboratory, Cold Spring Harbor, N.Y. (1981)); Ausbel, F. M., et al., Current Protocols in Molecular Biology, John Wiley and Sons, New York, N.Y., (1992); Glover, D., DNA Cloning, I and II (Oxford Press) (1985); Anand, Techniques for the Analysis of Complex Genomes, (Academic Press (1992)); Guthrie, G., et al., Guide to Yeast Genetics and Molecular Biology, (Academic Press (1991)); and Fink, et al., *Hum. Gene Ther.*, 3, 11–19 (1992).

The present invention provides a method of gene therapy in which GFAT activity or elevation of blood glucose level is suppressed through provision of an antisense drug for producing, in a cell in which the gene of the present invention is expressed, RNA having a sequence complementary to that of mRNA; inhibiting translation; and suppressing expression of the GFAT1L gene.

The above gene therapy method is a method for suppressing expression of the target gene by inhibiting a step of transcription or translation, the inhibition being attained, for example, by binding a proper mRNA in a GFAT expression cell containing the GFAT1L gene or forming a triple strand through interposition into the DNA double helix structure. This method is recognized as a method in which an antisense oligonucleotide complementary to mRNA of the gene is produced and the antisense oligonucleotide is transferred to a target cell.

If an action for suppressing the function for expressing the GFAT1L gene is provided, GFAT activity in a receptor cell/target cell or elevation of blood glucose level can be suppressed. By use of a vector or plasmid containing the antisense oligonucleotide, the oligonucleotide can be introduced into a target cell while it remains outside the chromosome.

According to the gene therapy for diabetes by use of the aforementioned antisense oligonucleotide, the antisense oligonucleotide is incorporated into retrovirus, adenovirus, or a vector originating from AAV, and GFAT activity-expressing cells are transfected with the virus or vector, to thereby excessively express the antisense oligonucleotide. Thus, a desired blood glucose level reduction effect can be attained.

In the case in which antisense oligonucleotide is introduced into a cell containing the GFAT1L gene so as to suppress expression of the GFAT1L protein, the antisense oligonucleotide is not necessarily identical to the entire length of the corresponding GFAT1L gene. For example, the aforementioned reformant and a gene comprising a partial sequence maintaining a specific function can also be used, so long as these species maintain a function substantially equivalent to the function for suppressing expression of the GFAT1L gene.

Such vectors for introducing a desired gene for the purpose of both recombination and maintenance outside the chromosome have already been known in the art, and any of these known vectors can be used in the present invention. Examples of the vectors include virus vectors and plasmide vectors which contain a copy of the antisense oligonucleotide of the GFAT1L linked to an expression control element and can express a product of the antisense oligonucleotide in a target cell. Although the aforementioned expression vector can be used as the above vector, original vectors such as vectors (e.g., pWP-7A, pWP-19, pWU-1, pWP-8A, pWP-21, and/or pRSVL) disclosed in U.S. Pat. No. 5,252,479 and PCT International Publication WO 93/07282 or vectors prepared by use of pRC/CMV (product of Invitrogen) are preferably used. More preferably, any of a variety of virus vectors described below is used.

Regarding the promoter to be used in vectors for use in gene transfer therapy, there can be preferably used a promoter specific to the diseased part tissue which is a target of therapy of diseases.

Specific examples of the promoter will be described. Examples of the promoter in relation to the skeletal muscle include skeletal muscle actin, a myosin heavy chain, and creatine kinase. Examples of the promoter in relation to the heart include atrial natriuretic hormone, a ventricle-specific myosine light chain, and atrial-specific and ventricular-specific $\alpha$-myosin heavy chains. Examples of the promoter in relation to the liver include albumin, $\alpha$-fetoprotein, $\alpha$1-antitrypsin, transferrin, and transstyrene. Examples of the promoter in relation to the colon include antigens such as carboxylic acid anhydrase I and carcino-embryonic antigen. Examples of the promoter in relation to the uterus and placenta include estrogen, aromatase cytochrome P450, cholesterol side-chain lyase P450, and 17$\alpha$-hydroxylase P450.

Examples of the promoter in relation to the prostate include a prostate antigen, the gp91-fox gene, and the prostate-specific kallikrein. Examples of the promoter in relation to the breast include erb-B2, erb-B3, $\beta$-casein, $\beta$-lactoglobin, and lactoprotein. Examples of the promoter in relation to the lung include activator protein C uroglobulin. Examples of the promoter in relation to the skin include K-14 keratin, human keratin 1 or 6, and leukorin.

Examples of the promoter in relation to the brain include grial fibrillary acidic protein, matured astrocyte-specific protein, myelin basic protein, and tyrosine hydroxylase. Examples of the promoter in relation to the spleen include villin, glucagon, Langerhans islet amyloid polypeptide, amylase, and PAP1. Examples of the promoter in relation to the thyroid gland include thioglobulin and calcitonin. Examples of the promoter in relation to the bone include $\alpha$1 collagen, osteocalcin, and bone sialoglycoprotein. Examples of the promoter in relation to the kidney include renin, liver/bone/kidney alkaline phosphatase, and erythropoetin.

During production of the vector for introducing antisense oligonucleotide, the antisense oligonucleotide to be introduced (the entirety or a portion of the complementary sequence corresponding to the sequence of the GFAT1L gene) can readily be produced and collected through a general genetic engineering method, as described above, based on the nucleotide sequence information of the gene of the present invention.

The vector for introducing the antisense oligonucleotide can be introduced into cells through any of a variety of methods already known in the field of DNA introduction to cells. Examples of the method include electroporation, calcium phosphate coprecipitation, and virus transduction. Cells per se transformed by the antisense oligonucleotide of the GFAT1L gene can also be utilized, in an as-isolated state, as a drug for suppressing GFAT activity or elevation of blood glucose level or as a model for studying therapy therefor.

In the gene therapy, the vector for introducing the aforementioned antisense oligonucleotide can be introduced to target cells of patients by injecting topically to a tissue site or by generally injecting. When the vector is generally injected, the vector can reach any cell which expresses GFAT mRNA in other sites. If permanent uptake of the transduced gene into the chromosome of each target cell cannot be attained, the injection may be repeated periodically.

The gene therapy of the present invention encompasses both an in vivo method in which a material for introducing the aforementioned antisense oligonucleotide (a vector for introducing antisense oligonucleotide) is administered directly to the body and an ex vivo method in which the target cell is removed from the patient's body, a gene is introduced into the cell outside the body, and the cell is transferred back to the body.

Alternatively, also applicable is gene therapy in which the antisense oligonucleotide of the GFAT1L gene is introduced directly into a cell and ribozyme—active molecule cutting the RNA chain—is used.

The below-described gene therapeutic drug of the present invention, which drug contains as active ingredients a vector for introducing a gene containing the entirety or a fragment of antisense oligonucleotide having a sequence corresponding to the GFAT1L gene of the present invention and a cell into which the antisense oligonucleotide of the human GFAT1L gene is introduced by the vector, is applied particular to diabetes as a target. However, in addition to diabetes, the aforementioned gene therapy (treatment) can also be carried out in order to treat diabetic complications such as diabetic neuropathy, diabetic nephropathy, and diabetic retinopathy and to label genetically.

The target cell to which antisense oligonucleotide is introduced can appropriately be selected in accordance with the gene therapy (treatment) target. Examples of the target cell—a cell in which expression of GFAT is confirmed—include, in addition to the skeletal muscle tissue and the heart tissue, lymphocyte, fibroblast, a liver cell, a hematinic stem cell.

The method of introducing antisense oligonucleotide in relation to the aforementioned gene therapy includes a method by use of a virus and a method without use of a virus.

Examples of method by use of a virus include a method in which a retrovirus vector is used as the vector, the method being based on the criterion that the antisense oligonucleotide of the GFAT1L gene is a foreign substance expressed in a normal cell. Examples of other virus vectors include an adenovirus vector, an HIV (human immunodeficiency virus) vector, an AAV (adeno-associated virus), a herpes virus vector, an HSV (herpes simplex virus) vector, and an EBV (Epstein-Barr virus) vector.

Examples of the method without use of a virus include a calcium phosphate co-precipitation method; a membrane fusion liposome method in which a liposome including DNA and Sendai virus which has been inactivated in advance through destruction by a UV ray are fused, to thereby produce a membrane-fused liposome, and the thus-formed liposome is directly fused to cell membrane, to thereby introduce DNA into a cell [Kato, K., et al., *J. Biol. Chem.*, 266, 22071–22074 (1991)]; a method for physically introducing DNA into a cell by subjecting gold-coated plasmid DNA to high-voltage electric discharge [Yang, N. S., et al., *Proc. Natl. Acad. Sci.*, 87, 9568–9572 (1990)]; a naked DNA method in which plasmid DNA is injected in vivo directly to an organ or a target tissue [Wolff, J. A., et al., *Science*, 247, 1465–1467 (1990)]; a cationic liposome method in which a gene embedded in a positively charged multilamellar liposome is introduced into a cell [Kunio Yagi, *Igaku no Ayumi*, Vol. 175, No. 9, 635–637 (1995)]; and a ligand-DNA complex method in which DNA is linked to a ligand bonding to a receptor which expresses in a target cell in order to introduce a gene exclusively into a specific cell and not into other cells and the thus-formed complex is administered [Frindeis, et al., *Trends Biotechnol.*, 11, 202 (1993)]; Miller, et al., *FASEB J.*, 9, 190 (1995)].

Examples of the aforementioned ligand-DNA complex method include a method employing asialoglycoprotein as a ligand and, as a target, an asialoglycoprotein receptor in which a liver cell expresses [Wu, et al., *J. Biol. Chem.*, 266, 14338 (1991); Ferkol, et al., *FASEB J.*, 7, 1081–1091, (1993)] and a method employing as a target a transferrin receptor in which a target cell strongly expresses, and transferrin as a ligand [Wagner, et al., *Proc. Natl. Acad. Sci.*, USA, 87, 3410 (1990)].

The method for introducing a gene into a cell employed in the present invention also encompasses an appropriate combination of the aforementioned biological and physical gene-introduction methods. Examples of such combined methods include a method in which plasmid DNA of a specific size is combined with a polylysine-conjugated antibody specific to adenovirus hexone protein. In this method, the formed complex is linked to an adenovirus vector, and a cell is transfected with the thus-formed trimolecular complex, to thereby introduce the antisense oligonucleotide of the present invention. In the method, effective linkage, endogenous inclusion, and decomposition of endosome can be attained before the DNA coupled with the adenovirus vector is damaged. The aforementioned liposome/DNA complex can directly mediate gene introduction in vivo.

The method of preparing a virus vector for introducing the antisense oligonucleotide of the present invention and the method for introducing the antisense oligonucleotide into a target cell and a target tissue will next be described specifically.

The retrovirus vector system comprises a virus vector and a helper cell (packaging cell). The term "helper cell" refers to a cell which has expressed a gene such as structural protein gag of retrovirus (structural protein in virus particles), pol (reverse transcriptase), or env (envelope protein) but has not formed virus particles. The virus vector includes a packaging signal and LTR (long terminal repeats), but does not contain a structural gene for replicating a virus such as gag, pol, or env. The packaging signal is a sequence serving as a tag during assembly of virus particles, and a selective marker (gene) (neo, hyg) and a desired introduction antisense oligonucleotide (total antisense oligonucleotide corresponding to GFAT1L or its fragment) incorporated into a cloning site are inserted instead of virus genes. In order to obtain high-titer virus particles, it is important to limit the length of insertion to as short as possible, to widen the packaging signal including a part of the gag gene, and to prevent ATG of the gag gene from remaining in there.

By transferring, to a helper cell, the vector DNA into which the antisense oligonucleotide of the desired GAFT1L gene is incorporated, vector genome RNA is packed with a virus structural protein which the helper cell produces, to thereby form virus particles in the helper cell and secrete the virus particles from the helper cell. After transfection of a target cell with the virus particles serving as recombinant virus particles, the DNA which is reverse-transcribed from the virus genome RNA is incorporated into the target cell nucleus, to thereby express the antisense gene inserted in the vector.

In order to enhance the efficiency of gene introduction, a method employing a fragment of fibronectin having a cell adhesion domain, a heparin-bonding site, and a conjugation segment [Hanenberg, H., et al., *Exp. Hemat.*, 23, 747 (1995)] can also be applied.

Examples of the vector used in the aforementioned retrovirus vector system include a retrovirus originating from a mouse leukemia virus [McLachlin, J. R., et al., *Proc. Natl. Acad. Res. Molec. Biol.*, 38, 91–135 (1990)].

The method for employing adenovirus vector will next be described in detail. The adenovirus vector can be prepared in accordance with a method described by Berkner, K. L. [*Curr. Topics Microbiol. Immunol.*, 158, 39–66 (1992)]; Setoguchi, Y., et al. [*Blood*, 84, 2946–2953 (1994)]; Hiromi Kanegae, et al. [*Jikken Igaku*, 12, 28–34 (1994)]; or Ketner, G., et al [*Proc. Natl. Acad. Sci.*, USA, 91, 6186–6190 (1994)].

For example, in order to prepare non-growth adenovirus vector, the E1 and/or E3 regions of an initial gene of the adenovirus are removed. Then, a cell; e.g., a 293 cell, is transfected simultaneously with a plasmid vector containing a desired target external gene-expressing unit (comprising a target introduction antisense oligonucleotide; i.e., the antisense oligonucleotide of the GAFT1L gene of the present invention; a promoter for transcripting the antisense oligonucleotide; and poly-A for imparting stability to the transcripted gene) and a portion of adenovirus genome DNA, and a plasmid containing an adenovirus genome. Two species undergo homologous recombination for substituting the gene-expressing unit by E1 or vise versa, to thereby prepare a non-growth adenovirus vector—a vector embedding the antisense oligonucleotide of the desired GFAT1L gene. In addition, end-protein-added 3'-side adenovirus vector can also be prepared by incorporating adenovirus genome DNA into a cosmid vector. Furthermore, a YAC vector can be used for preparing a recombinant adenovirus vector.

Production of an adeno-associated virus (AAV) vector will be generally described. AAVs were found as small viruses which were mingled into a culture system of adenovirus. Among AAVs, existence of he following two groups have been confirmed: Parvoviridae which proliferates in a self-controlled manner in a host cell without requiring a helper virus for virus replication and Dependoviridae which requires helper virus for replication. The AAVs, which are a common virus having a wide host-range, easily transfect a variety of cells. Each virus genome consists of a linear single-strand DNA having 4680 nucleotides, and 145 nucleotides of each end have a characteristic sequence, called ITR (inverted terminal repeat). The ITR serves as a replication-initiating point and functions as a primer. In addition, the ITR is essential for packaging AAV into virus particles and incorporating AAV into chromosomal DNA of a host cell. Regarding the virus protein, the left half of the genome is formed of a non-structural protein. Thus, the virus protein encodes Rep—regulatory protein responsible for replication and transcription.

The recombination AAV can be produced on the basis of a property that the AAV is introduced into chromosomal DNA, to thereby produce a desired vector for gene introduction. More specifically, in this method, a plasmid (AAV vector plasmid) in which a desired introduction antisense oligonucleotide (antisense oligonucleotide of the GFAT1L gene) is inserted between 5' and 3' ends of wild-type AAV, while the ITR at each end remains, is produced. In contrast, a virus protein required for replication of the virus and formation of the virus particles is supplied by use of another helper plasmid. These two plasmids must be provided such that the plasmids have no common nucleotide sequence and that no recombinant wild-type virus emerges. Subsequently, these plasmids are introduced to a cell such as 293 cell through transfection, and the transfected cell is further transfected by an adenovirus (non-growth type virus is acceptable when 293 cell is used) serving as a helper virus, to thereby produce a desired non-growth type recombinant AAV. Since the thus-produced recombinant AAV remains in the cell nucleus, the recombinant AAV is collected by freeze-thawing the relevant cells, and the intermingled adenovirus is inactivated by heating at 56° C. Optionally, the recombinant AAV is separated and concentrated through ultracentrifugation by use of cesium chloride. In the aforementioned manner, a desired recombinant AAV for gene introduction can be obtained.

The EBV vector can be produced in accordance with a method, for example, described by Norio SHIMIZU et al. [*Cell Engineering*, 14(3), 280–287 (1995)].

The method for producing an EBV vector for introducing the antisense oligonucleotide of the present invention will be described generally. The EB virus (Epstein-Barr virus: EBV) is a virus which belongs to Herpesviridae and was first isolated in 1964 by Epstein et al. from cultured cells originating from Burkitt lymphoma [Kieff, E. and Liebowitz, D.: Virology, 2nd ed., Raven Press, New York, 1990, pp. 1889–1920]. Since the EBV has an activity for transforming a cell, a virus lacking the transform activity must be prepared in order to form a vector for introducing a gene. The preparation can be carried out in the following manner.

Specifically, an EBV genome in the vicinity of a target DNA to which a desired external gene is to be introduced is cloned. To the cloned genome, a DNA fragment of the external gene and a drug-resistant gene are introduced, to thereby form a vector for producing a recombinant virus. Subsequently, an EBV-positive Akata cell is transfected by the vector for producing a recombinant virus and cleaved by an appropriate restriction enzyme. The recombinant virus formed through homologous recombination is subjected to stimulation for virus-production generated through anti-surface immunogloblin treatment, and is collected together with a wild-type Akata EBV. An EBV-negative Akata cell is transfected with the virus mixture, and a resistant-strain is selected in the presence of a drug, to thereby obtain an Akata cell which is transfected exclusively by the desired recombinant virus including no wild-type EBV. Furthermore, by imparting a virus activity to the recombinant virus-transfected Akata cell, the target recombinant virus vector can be produced in a large amount.

The non-virus vector, which can introduce a desired antisense oligonucleotide into a target cell without using a recombinant virus vector, is produced through a method such as gene introduction by use of a membrane-fused liposome. This method introduces the content of the liposome directly into a cell by imparting, to a membrane liposome (vesicle formed of lipid bilayer), activity of fusion to cell membrane.

Introduction of the antisense oligonucleotide by use of the aforementioned membrane-fused liposome is performed, for example, through a method described by Nakanishi, M., et al. [*Exp. Cell Res.*, 159, 399–499 (1985); and Gene Introduction into Animal Tissues, in Trends and Future Perspectives in Peptide and Protein Drug Delivery (ed. by Lee, V. H. et al.)., Harwood Academic Publishers Gmbh. Amsterdam, 1995, pp. 337–349].

The method for introducing the antisense oligonucleotide by use of membrane-fused liposome will be described generally. Specifically, Sendai virus, the gene of which is deactivated by a UV ray, and a liposome into which polymer substances such as a desired antisense oligonucleotide and expression protein are included are fused at 37° C. The thus-formed membrane-fused liposome includes, in an inner portion, a cavity originating from the non-fused liposome and, in an external portion, a spike similar to that of a virus envelope. Thus, the membrane-fused liposome has a pseudo-virus structure. The membrane-fused liposome is further purified through sucrose density-gradient centrifugation and, subsequently, adsorbed on a target cultured cell or tissue cell at 4° C. By elevating the temperature to 37° C., the content of the liposome is introduced into the cell. Thus, the desired antisense oligonucleotide can be introduced into a target cell. The lipid employed as liposome is preferably a synthetic phospholipid containing 50% (mol) cholesterol and lecithin and negatively charged and is preferably formed into monolamellar liposome having a diameter of 300 nm.

In order to introduce the antisense oligonucleotide into a target cell by use of another liposome, there can be applied an antisense oligonucleotide introduction method making use of a cationic liposome. This method is executed in accordance with a method described by Yagi et al. [B.B.R.C., 196, 1042–1048 (1993)]. This method is based on the fact that plasmids and cells are both negatively charged, and imparts positive charge to both inner and outer surfaces of the liposome membrane and promotes uptake of plasmid by electrostaticity, to thereby enhance interaction to a cell. The liposome employed herein is preferably a positively charged large multi-lamellar liposome (multilamellar large vesicles: MLV). However, a desired antisense oligonucleotide can also be introduced by preparing a complex of plasmid and a large uni-lamellar liposome (large unilamellar vesicles: LUV) or a small uni-lamellar liposome (large unilamellar vesicles: SUV).

The method for preparing plasmid-embedded cationic MLV will be described generally. Specifically, lipid TMAG (N-(α-trimethylammonioacetyl)-didodecyl-D-glutamate chloride), DLPC (dilauroyl phosphatidylcholine), and DOPE (dioleoyl phosphatidylethanolamine) are dissolved in chloroform so as to prepare a solution containing these three components in molar proportions of 1:2:2 (lipid concentration 1 mM). Subsequently, a portion of the solution, which contains 1 μmol of lipids in a total amount, is placed in a Spitz test tube, and chloroform is removed through distillation under reduced pressure by means of a rotary evaporator, to thereby prepare lipid thin film. Remaining chloroform is further removed under reduced pressure, and the film is dried. Then, Dulbecco phosphoric acid buffered saline (Mg, Ca-added) (0.5 ml) containing plasmid for gene introduction (20 μg) is added to the lipid film, and the atmosphere is purged with nitrogen gas. The mixture is stirred for two minutes by means of a vortex mixer, to thereby yield plasmid-embedded cationic MLV suspension containing the desired antisense oligonucleotide.

The thus-obtained plasmid-embedded cationic MLV can be used as a gene-therapeutic drug. For example, an expression plasmid into which a target antisense oligonucleotide to be expressed is introduced is embedded in the aforementioned cationic MLV such that the amount of DNA and that of liposome lipid are controlled to 0.6 μg and 30 nmol, respectively. The thus-obtained plasmid-embedded cationic MLV is suspended in a phosphoric-acid-buffered saline (2 μl). The suspension is administered to a target cell extracted from a patient or to tissue of a patient at one-day intervals.

The term "gene therapy" is defined in the guideline by Ministry of Health and Welfare (Japan) as "administration of a gene or a gene-transferred cell to the human body in order to treat a disease." However, in addition to the above definition from the guideline, the gene therapy according to the present invention encompasses a therapy for diabetes and complications thereof by transferring, to the aforementioned target cell, an antisense oligonucleotide characterized by the GFAT-expression-suppressing antisense DNA of the GFAT1L gene. The gene therapy also includes introduction, to the human body, of a marker gene or a cell into which the marker gene is transferred.

In the gene therapy of the present invention, examples of typical methods for transferring a desired gene into a target cell or tissue include the following two methods.

The first method is a gene transfer method in which a target cell or tissue of a patient is transfected directly by a virus vector such as an adenovirus vector into which a target antisense oligonucleotide (antisense oligonucleotide of the GFAT1L gene) has been introduced.

Alternatively, as a variation of the first method, there may be employed an ex vivo method in which a cell derived from a patient is transfected by a virus vector containing a target antisense oligonucleotide (antisense oligonucleotide of the GFAT1L gene) or is co-cultured with a virus-producing cell containing the virus vector, to thereby introduce the target antisense oligonucleotide to the target cell and transplant the cell into the patient's body.

The second method is a direct gene transfer method (direct method) in which an antisense oligonucleotide (antisense oligonucleotide of the GFAT1L gene) that is incorporated into an appropriate target animal-cell-expression vector plasmid DNA is injected directly to a target site of a patient; e.g., the body or the skeletal muscle. The injection can be carried out through a method such as an HVJ liposome method, a cationic liposome method, direct DNA injection, electroporation, or a gene gun method.

When the aforementioned methods are carried out, preferably confirmation is made in advance as to whether or not the target antisense oligonucleotide (antisense oligonucleotide of the GFAT1L gene) is actually introduced, particularly through an in vitro preliminary test such as PCR retrieval of a vector gene cDNA or in situ PCR. Alternatively, preferably confirmation is made of increase or decrease in the specific activity—a desired therapeutic effect attributed to transfer of the target antisense oligonucleotide (antisense oligonucleotide of the GFAT1L gene)—and the effect to the target cell. Needless to say, when the gene therapy employing an virus vector is carried out, it is important to confirm the safety in relation to transfer of an antisense oligonucleotide thereof, on the basis of PCR retrieval of a proliferation virus.

The present invention also provides a drug composition or a drug preparation (gene-therapeutic agent) comprising, as an active ingredient, a vector for transferring the antisense oligonucleotide of the present invention or a cell into which the target antisense oligonucleotide (antisense oligonucleotide of the GFAT1L gene) is introduced in a pharmaceutically effective amount, and an appropriate non-toxic drug carrier or diluent.

Examples of the drug carrier which can be used in the aforementioned drug composition (drug preparation) include typically employed diluents and vehicles, in accordance with the form of use of the preparation. Specific examples include a filler, a bulking agent, a binder, a moisturizer, a disintegrant, a surfactant, and a lubricant, and the carrier is appropriately selected and used in accordance with the form of administration of the preparation to be produced.

Examples of the form of administration of the preparation include those described in relation to the aforementioned GFAT1L protein antibody preparation, and the. form is appropriately selected from a variety of forms in accordance with the target of therapy.

For example, a drug preparation containing a vector for introducing the antisense oligonucleotide of the present invention is prepared as the vector embedded in a liposome or a cultured cell transfected by a virus containing a virus vector including a desired antisense oligonucleotide.

These preparations may be added to a phosphoric acid-buffered saline (pH 7.4), Ringer solution, intracellular composition fluid for injection, etc. Alternatively, these preparations may be administered in combination with a substance such as protamine which enhances the efficiency of gene transfer.

The method for administering the aforementioned drug preparation is not particularly limited, and is determined in accordance with conditions such as the form of the drug preparation, the age, sex, and other conditions of a patient, and the gravity of the disease.

The amount of the active ingredient to be incorporated into the aforementioned pharmaceutical composition and the dose of the composition are not particularly limited, and they are appropriately determined in a wide range in accordance with therapeutic effect desired, manner of administration, period of therapy, patient's age and sex, and other conditions.

The pharmaceutical composition can be administered once a day, or the daily dose can be divided into several times. Also, the composition can be administered intermittently at one- to several-week intervals. Preferably, protamine or a similar substance that enhances the efficiency of gene transfer, or a composition containing such a substance, is administered in combination with the pharmaceutical composition.

When the gene therapy according to the present invention is applied to the therapy of diabetes, different types of gene therapy as described above may be appropriately combined (combined gene therapy). Also, the aforementioned gene therapy may be combined with conventional insulin therapy, trophotherapy, etc. Moreover, the gene therapy of the present invention may be performed, including safety of the therapy, with reference to the guidelines by NIH (Recombinant DNA Advisory Committee, Human Gene Therapy, 4, 365–389 (1993)).

According to the present invention, the presence of the GFAT1L gene—which elicits cellular GFAT activity—can be detected by preparing a biological sample such as blood or serum, extracting nucleic acid as needed, and confirming the presence of a GFAT1L-sensitive gene. Also, according to the present invention, GFAT activity level and GFAT mRNA expression level in cells or tissue, as well as an index of progress or prognosis of hexosamine biosynthesis pathway regulatory dysfunction, can be determined by preparing a biological sample involving hexosamine biosynthesis pathway regulatory dysfunction, and detecting the presence of GFAT1L gene or determining the amount of the mRNA thereof. Employment of such a method of the present invention enables detection of the level of GFAT activity in cells or tissue and the expression level of GFAT mRNA, as well as identification of an index of progress or prognosis of hexosamine biosynthesis pathway regulatory dysfunction, and thus realizes diagnosis of the mentioned dysfunction (e.g., diabetes), determination of therapeutic effects on diabetes, and prediction of prognosis of therapy for diabetes.

According to the detection method, on the basis of information regarding the GFAT1L gene obtained from a patient's sample which has previously been confirmed to exhibit GFAT activity, a DNA fragment is designed and prepared for use in the screening for GFAT1L gene and/or amplification of the gene. More specifically, there can be designed and prepared a fragment serving as a probe employable in plaque hybridization, colony hybridization, southern blotting, northern blotting, etc., or a fragment serving as a probe employable for obtaining the entirety, or a portion, of the DNA fragment of GFAT1L which has been amplified through polymerase chain reaction (PCR) in which a nucleic acid sequence is amplified with polymerase. To this end, the first step is to prepare a primer having a sequence identical to the sequence of GFAT1L. The resultant primer is used as a probe for screening and is reacted with a biological sample (nucleic acid sample). Thus, the presence of a gene having the GFAT1L sequence can be confirmed. The nucleic acid sample may also be prepared through any of a variety of methods that facilitate detection of a target sequence, such as denaturation, restriction enzyme digestion, electrophoresis, dot blotting, etc.

From the viewpoint of sensitivity, the screening method is preferably PCR. PCR is not particularly limited so long as it employs a GFAT1L fragment as a primer, and there can be employed a conventionally known method (Science, 230, 1350–1354 (1985)) or modified PCR which has newly been developed (or which will be used in future) ("*Jikken Igaku*" special issue, 8(9) (1990), edited by Yoshiyuki Sakaki et al., published by Yodosha; "*Tanpakushitu, Kakusan, Koso*" 35(17) (1990), extra edition, published by Kyoritsu Shuppan K.K.).

The DNA fragment to. be. used as a primer is a chemically synthesized oligo DNA, and can be synthesized by means of an automated DNA synthesizer; e.g., a DNA synthesizer "PharmaciaLKB Gene Assembler Plus" (product of Pharmacia). The length of the thus-synthesized primer (a sense primer or an antisense primer) is preferably about 10 to 50 nucleotides, more preferably 15 to 30 nucleotides. In this connection, the primer to be synthesized is preferably a sequence that can be distinguished from the DNA sequence of any other known GFAT. Generally, the probe used in the aforementioned screening is a labeled probe. However, the probe may be unlabeled, and may be detected, directly or indirectly, on the basis of specific binding with a labeled ligand. Suitable labeling species and suitable method for labeling a probe or ligand are known in the technical field of the present invention. For example, there may be used radioactive labeling substances, biotin, fluorophores, chemiluminescence moieties, enzymes, antibodies, or similar substances which can be incorporated into the probe or ligand through a known method such as nick translation, random priming, or treatment with kinase.

The PCR method to be used for the purpose of detection may be so-called RT-PCR, and a variety of modified PCR methods may also be employed.

Moreover, the assay method of the present invention may be performed easily and conveniently by using a reagent kit for detecting the GFAT1L gene in a specimen.

Accordingly, the present invention provides a reagent kit for detecting GFAT1L, characterized in that the kit contains the aforementioned GFAT1L DNA fragment.

The reagent kit comprises, as an essential element therefor, a DNA fragment that hybridizes with the entirety, or a portion, of the nucleotide sequence shown as SEQ ID NO: 2 or a complementary nucleotide sequence thereof. The kit may contain other elements, such as a labeling agent and a reagent that is essential to PCR (e.g., Taq DNA polymerase, deoxynucleotide triphosphate, primer, etc.) as optional elements.

Examples of the labeling agent include chemically modifying substances such as radioisotopes and phosphors. The DNA fragment per se may be conjugated with the labeling agent in advance. Moreover, for the sake of assay convenience, the reagent kit may include suitable materials such as a diluent, a standard antibody, buffer, detergent, and a reaction stopping solution.

The present invention also provides a method for diagnosing glucose metabolism disorder; in particular, hexosamine biosynthesis dysfunction, by use of the above-described assay method; a diagnosis agent to be used in the method; and a diagnosis kit.

When the above-described assay method is used, GFAT1L obtained from a test specimen can be sequenced directly or indirectly, thereby facilitating identification of a related gene; i.e., a gene related to a new GFAT1L gene, which is a high-homology homologue to wild-type GFAT1L.

Thus, the present invention also provides a screening method for a human GFAT1L related gene in a test specimen, which method comprises the above described assay method and sequencing of the GFAT1L DNA in the test specimen.

By use of the polypeptide of SEQ No. 2 of the present invention which is encoded by the human GFAT1L gene, an amino acid sequence of SEQ No. 2 wherein one to several amino acids have been deleted, substituted, or inserted, or a fragment thereof, it is possible to synthesize a polypeptide, or an antibody for the polypeptide, enabling an assay for wild-type GFAT1L and/or mutated GFAT1L.

Accordingly, the present invention provides an assay method for an anti-wild-type-GFAT1L antibody and/or anti-mutated-GFAT1L antibody, as well as an assay method for corresponding antigens. By use of the assay methods of the present invention, the following can be determined on the basis of changes in wild-type GFAT1L polypeptide: the level of GFAT activity, degree of glucose regulatory dysfunction, severity of hexosamine biosynthesis pathway dysfunction, gravity of diabetes, and severity of diabetic complications such as diabetic neurosis, diabetic retinopathy, diabetic nephropathy, etc. Although such changes may be determined by sequencing GFAT1L through the aforementioned customary techniques in the art, preferably, an antibody (either polyclonal or monoclonal) is used so as to detect any difference present in a GFAT1L polypeptide or the presence or absence of a GFAT1L polypeptide. In a specific example assay method of the present invention, GFAT1L antibodies cause immunoprecipitation of GFAT1L protein from a liquid containing a biological sample collected from a human, such as blood or serum, and react with GFAT1L polypeptide when western blotting or immunoblotting is performed on polyacrylamide gel. The GFAT1L antibody also allows for detection of GFAT1L polypeptide contained in a paraffin-embedded slice or frozen tissue slice, by use of immunohistochemical techniques. Techniques for producing and purifying an antibody are well known in the art, and thus a suitable technique can be suitably chosen from among them.

Specific examples of preferred methods which are employable in relation to detection of wild-type GFAT1L or its variant include enzyme-linked immunosolbent assay (ELISA), radioimmunoassay (RIA), immunoradiometric assay (IRMA), and immunoenzymemetric assay (IEMA) on the basis of a sandwich method using a monoclonal antibody and/or a polyclonal antibody.

In one possible embodiment of the screening method of the present invention for screening for a candidate compound that serves as a GFAT-activity-inhibitory drug, GFAT1L protein or a partial peptide thereof is quantitatively determined. Briefly, an antibody against a GFAT1L gene expression product or GFAT1L protein (hereinafter these two will be collectively referred to as GFAT1L protein) or a fragment thereof is subjected to competitive reaction with a test fluid containing a candidate compound and with labeled GFAT1L protein or a partial peptide thereof, and the amount of labeled GFAT1L protein or partial peptide thereof that is caused to be bound to the antibody is measured.

The following assay for quantitative determination of GFAT1L protein or a partial peptide thereof contained in a test fluid is also possible: A test fluid containing a candidate compound is subjected to reaction with an antibody immobilized onto a carrier and with another antibody which is labeled and which is against GFAT1L protein in a simultaneous or sequential manner.

According to another possible method of screening for compounds which inhibit enzymatic activities (e.g., GFAT activity) of GFAT1L protein or a partial peptide thereof, for the following two cases of a substrate being brought into contact with the GFAT1L protein or partial peptide thereof and both a substrate and a test compound being brought into contact with the GFAT1L protein or partial peptide thereof, enzymatic activity of the GFAT1L protein or partial peptide thereof is measured and the results are compared with each other.

In the above method, the substrate is not particularly limited, so long as it can serve as a substrate for the protein of the present invention or a partial peptide of GFAT1L protein. Typically, fructose-6-phosphate or glutamine is employed. When fructose-6-phosphate is used, radioisotope-labeled (e.g., with 14C, 3H, etc.) fructose-6-phosphate is preferably employed. Examples of the test compound include, but are not limited to, peptides, proteins, non-peptic compounds, synthesized compounds, fermentation products, cell extracts, plant extracts, animal tissue extracts, and blood. The mentioned compounds may be either novel compounds or known compounds.

In carrying out any of the screening methods described above, the protein of the present invention or a partial peptide of GFAT1L protein is suspended in a buffer which is suitable for the screening purposes, to thereby prepare a sample of the protein or the partial peptide. Any buffer having a pH of approximately 4 to 10 (preferably approximately 6 to 8), such as phosphate buffer, Tris-HCl buffer, etc., can be used, so long as it does not inhibit binding of the protein of the present invention or a partial peptide of GFAT1L protein to the substrate.

The GFAT activity of the protein of the present invention or a partial peptide of GFAT1L protein can be measured through a known method; e.g., in accordance with a method disclosed by Marshal et al. (Journal of Biological Chemistry, vol. 266, No. 8, 4706–4712 (1991).

For example, appropriately diluted GFATI-L expressed $E.$ $coli$ lysate (50 μl) is added to 200 μl of a substrate solution (400 mM sodium phosphate buffer (pH 7.5), 50 mM potassium chloride, 1.25 mM EDTA, 0.3 mM APAD, 6 U/ml glutamate dehydrogenase (GDH), 0–6 mM glutamine, 0–6 mM fructose-6-phosphate (F-6-P)), and the resultant solution is placed in wells of a 96-well microplate, thereby allowing reaction for 60 minutes at 37° C. Changes in absorbance at 365 nm are measured by use of a microplate reader. According to the thus-performed GFAT activity assay, glutamate produced by GFAT is further reacted with glutamate dehydrogenase (GDH). During the reaction, APAD (a coenzyme) is simultaneously generated, and changes in absorbance that accompany the reduction reaction of APAD to APADH are considered to represent GFAT activity.

Alternatively, a method described by Smith et al. (Analytical Biochemistry, 98, 478–480, 1979) may be carried out. This method proceeds as follows. Briefly, the protein of the present invention or a partial peptide of GFAT1L protein is added to a mixture containing 12 μM fructose-6-phoaphate, 5 μM glutamine, and 0.2 M phosphate buffer (pH 8.0), and the resultant solution is maintained at 25° C. for 30 minutes.

0.5 M HCl is added to the solution, and reaction is allowed to proceed for 2 hours at 98° C. Thereafter, 2.5% $NaNO_2$ and 12.5% $NH_4O_3NH_2$, then 0.25% 2-methyl-2-benzothiazolone, are added. Subsequently, 0.5% $FeCl_3$ is added, and the resultant solution is assayed for absorbance at 650 nm, to thereby quantitatively determine the produced glucosamine-6-phosphate.

In each of the above-described methods, selection of drug candidate compounds may be carried out as follows. For example, in the case in which GFAT activity as measured when the aforementioned test compound is not added is inhibited about 20% or more, preferably about 30% or more, more preferably about 50% or more, as compared with the case in which the test compound is added, the test compound is selected as a compound that inhibits GFAT activity of the protein of the present invention or a partial peptide of GFAT1L protein.

According to the present invention, there is provided a screening kit for screening for a candidate compound serving as a drug which inhibits the aforementioned GFAT activity.

The screening kit of the present invention contains, as an element thereof, the protein of the present invention or a partial peptide of GFAT1L protein. A specific example of the screening kit of the present invention will be described hereunder.

1. Screening Kit I

[Screening reagent]

1) GFAT1L sample: 50 μl GFAT1-L expressed *E. coli* lysate (partial peptide of GFAT1L protein)

2) Co enzyme-containing buffer: 400 mM sodium phosphate buffer (pH 7.5), 50 mM potassium chloride, 1.25 mM EDTA, 0.3 mM APAD, 6 U/ml glutamate dehydrogenase (GDH)

3) Substrate: 0–6 mM fructose-6-phosphate, 0–6 mM glutamine

For detection, absorbance at 365 nm is measured. [Assay method] Appropriately diluted GFAT1-L expressed *E. coli* lysate (50 μl) is added to 200 μl of a substrate solution (400 mM sodium phosphate buffer (pH 7.5), 50 mM potassium chloride, 1.25 mM EDTA, 0.3 mM APAD, 6 U/ml glutamate dehydrogenase (GDH), 0–6 mM glutamine, 0–6 mM fructose-6-phosphate (F-6-P)), and the resultant solution is placed in wells of a 96-well microplate, thereby allowing reaction for 60 minutes at 37° C. By use of a microplate reader, changes in absorbance at 365 nm are determined.

2. Screening Kit II

[Screening Reagent]

1) Protein sample: Protein of the present invention (partial peptide of GFAT1L protein) or a salt thereof 2) Buffer: 0.2 M sodium phosphate buffer (pH 8.0)

3) Substrate: 12 μM fructose-6-phosphate, 5 μM glutamine

For detection, absorbance at 650 nm is measured. [Assay method] A test compound is added to a reaction mixture containing 12 μM fructose-6-phosphate, 5 μM glutamine, protein of the present invention (or a salt thereof), and 0.2 M sodium phosphate buffer (pH 8.0), and the resultant mixture is maintained at 25° C. for 30 minutes. 0.5 M HCl is added thereto, to thereby effect hydrolysis for 2 hours at 98° C. 2.5% $NaNO_2$ and 12.5% $NH_4O_3NH_2$ are added thereto, and thereafter, 0.25% 2-methyl-2-benzothiazolone is added. Subsequently, 0.5% $FeCl_3$ is added, and the resultant solution is assayed for absorbance at 650 nm.

The compound or a salt thereof obtained by use of the screening method of the present invention or the screening kit of the present invention is a compound selected from the above-described test compounds (for example, peptides, proteins, non-peptide compounds, synthesized compounds, fermentation products, cell extracts, plant extracts, animal tissue extract), and inhibits enzymatic activity (e.g., GFAT activity) of the protein of the present invention (a partial peptide of GFAT1L protein). These compounds may be either novel compounds or known compounds. The candidate compound of ameliorating hypoglycemia is a compound which promotes enzymatic activity (e.g., GFAT activity) of the protein of the present invention (a partial peptide of GFAT1L protein)

Examples of the salt of such a compound include salts formed between the compound and a physiologically acceptable acid (such as inorganic and organic acid) or between the compound and a base (such as an alkaline metal). Acid-addition salts wherein the acid is physiologically acceptable acid is particularly preferred. Examples of the salts include, but are not limited to, salts formed between the compound and inorganic acid (e.g., hydrochloric acid, phosphoric acid, hydrobromic acid, sulfuric acid) and salts formed between the compound and organic acid (e.g., acetic acid, formic acid, propionic acid, fumaric acid, maleic acid, succinic acid, tartaric acid, citric acid, malic acid, oxalic acid, benzoic acid, methanesulfonic acid, and benzenesufonic acid).

The compound or a salt thereof which inhibits enzymatic activity of the protein of the present invention (including a partial peptide of GFAT1L protein; hereafter the same meaning applies) is useful as a therapeutic or preventive drug against, among others, diabetes and complications of diabetes.

The compound or a salt thereof which promotes enzymatic activity of the protein of the present invention is useful as a therapeutic or preventive drug against, among others, hypoglycemia and complications of hypoglycemia.

According to the present invention, it is possible to prepare polypeptides or structural analogues—such as GFAT1L agonists, GFAT1L antagonists, GEAT1L inhibitors—in order to develop a drug which enhances, or impedes, the in vivo functions of GFAT1L protein, or a GFAT1L protein derivatives in more active or stable form. The structural analogue can be determined in such a way that the three-dimensional structure of a protein complex formed, for example, between GFAT1L and another protein is subjected to X-ray crystallography, computer modeling, or a combination of them. Information regarding the structure of the structural analogue can also be obtained through modeling of protein on the basis of the structure of a homologous protein.

An example method for obtaining a GFAT1L protein derivative in more active or more stable form is alanine scanning. According to alanine scanning, a certain amino acid residue is substituted by Ala, and its effect on peptide activity is measured. Thus, similar analysis on respective amino acid residues of the peptide facilitates to determine a region which is critical to the activity and stability of the peptide. Through use of this method, more active GFAT1L protein derivatives or more stable GFAT1L protein derivatives can be designed.

It is also possible to isolate the marker-specific antibody selected by the employment of the functionality assay, and to analyze the crystal structure of the antibody. This approach typically provides a pharmacore which serves as a basis for subsequent pharmaceutical design. Production of anti-idiotype antibody against an antibody which is functional and pharmaceutically active enables identification or isolation of a peptide from a peptide bank of chemically or biologically produced peptides. Thus, the selected peptide is predicted to also serve as a pharmacore.

Thus, it is possible to design and develop drugs which have improved GFAT1L activity or stability, and which have different functions as, for example, inhibitors, agonists, or antagonists.

The cloned GFAT1L sequence realizes analytical study, such as X-ray crystallography, on GFAT1L protein when a sufficient amount of GFAT1L protein is procured. Moreover, GFAT1L protein ford of the amino acid sequence represented by SEQ ID NO: 2 is applicable to computer-modeling techniques in place of X-ray crystallography or in addition to X-ray crystallography.

Furthermore, according to the present invention, a GFAT1L-gene-knock-out mouse or a GFAT1L-gene-knock-in mouse (mutated mouse) can be created, and such a mouse can be used for identification of the site, within the GFAT1L gene sequence, which affects the aforementioned various GFAT1L activities; or in other words, functions of GFAT1L gene products or variants of GFAT1L gene products exhibited in the living body.

This method is drawn to a technique in which, making use of homologous recombination of a gene, genetic information of a living body is intentionally modified, and in one exemplary method, mouse embryonic stem cells (ES cells) are employed (Capeccchi, M. R., Science, 244, 1288–1292 (1989)).

In this connection, the method for creating the aforementioned mutated mouse has now become a routine method among skilled artisans in the art. Through combination of a suitable modification of this technique (as described in "Jikken Igaku," special issue, 14 (20), 1996; edited by Testuo Noda, published by Yodosha) with human wild-type GFAT1L gene or mutated GFAT1L gene, a mutated mouse can be easily created. Thus, design and development of drugs which have improved GFAT1L activity or stability, and which have different functions as, for example, inhibitors, agonists, or antagonists can be realized.

EXAMPLES

The present invention will next be described in more detail by way of examples.

Example 1

Cloning of GFAT1L and construction of an expression vector In order to construct an expression vector for known human GFAT (G. L. McKnight et al., J. Biol. Chem., 267, 25208–25212 (1992)), four primers P1–P4 were synthesized on the basis of the sequence of the human GFAT cDNA. The nucleotide sequences of these primers are represented by SEQ ID NOs: 3–6.

P1 corresponds to the nucleotide sequence from the 34th to the 66th nucleotides of SEQ ID NO: 1. P2 corresponds to the nucleotide sequence from the 16th to the 48th nucleotides of SEQ ID NO: 1. P3 corresponds to the nucleotide sequence from the 1st to the 30th nucleotides of SEQ ID NO: 1. P4 corresponds to the nucleotide sequence from the 2077th to the 2097th nucleotides of SEQ ID NO: 1. In order to enhance the expression efficiency in E. coli cells and to enhance the efficiency of codon substitution, variation was introduced into P1–P3, which are forward primers, at the following positions. P1: the 6th, 9th, 12th, 13th, 15th, and 18th nucleotides of SEQ ID NO: 3. P2: the 7th, 9th, 18th, 24th, 27th, 30th, 31st, and 33rd nucleotides of SEQ ID NO: 4. P3: the 22nd, 32nd, and 34th nucleotides of SEQ ID NO: 5.

A portion of nucleotide sequence P3 corresponding to the sequence from the 1st to the 10th nucleotides of SEQ ID NO: 5 was added so as to introduce the NdeI site (CATATG), which is necessary for effecting insertion into a pET vector. P4 is a reverse primer including an XhoI site (CTCGAG; refer to the sequence from the 1st to the 11th nucleotides of SEQ ID NO: 6) subsequent to the C-terminal amino acid residue. The primer was designed so that a stop codon (TAA) is inserted immediately before the XhoI site.

The following method enables construction, by use of the aforementioned four primers, of a vector in which codons are replaced by those which facilitate synthesis of the N-terminal amino acid residue in E. coli cells.

A reverse transcription reaction was effected on the basis of human skeletal muscle mRNA (purchased from Clontech Co., Ltd.) by use of primer P4 and reverse transcriptase. The human skeletal muscle mRNA (2 μg/μl) was denatured at 100° C. for five minutes, followed by rapid cooling on ice. To the mixture were added Tris hydrochloric acid (pH=8.3; 50 mM), potassium chloride (40 mM), magnesium chloride (6 mM), 1 mM DTT, primer 4 (0.1 mM), BSA (0.1 mg), MMLV reverse transcriptase (product of GIBCO BRL Co., Ltd.: 400 units/2 μl), and deionized water (DDW), to thereby yield a final volume of 50 μl, and the mixture was allowed to react at 37° C. for ten minutes.

The reaction product (5 μl) was denatured at 100° C. for five minutes, followed by PCR reaction by use of primers P1 and P4 in the following manner. To the product of the reverse transcription reaction (5 μl) were added a 10×buffer (5 μl), 2 mM mixture of dNTPs (5 μl), both of the primers (0.4 μM each), magnesium chloride (1 mM), KOD dash (2.5 units), and DDW, to thereby yield a final volume of 50 μl. The 10×buffer contained Tris hydrochloric acid (pH=8.0; 1.2 mM), potassium chloride (100 mM), ammonium sulfate (60 mM), Triton X-100 (1%), and BSA (0.1 mg/ml). The thus-obtained mixture was allowed to react through 30 reaction cycles each consisting of 95° C. for 30 seconds, 65° C. for 2 seconds, and 74° C. for 60 seconds; followed by 74° C. for five minutes.

The thus-obtained product (5 μl) was subjected to PCR under conditions similar to those described above, except that primers P2 and P4 were used.

The thus-obtained product (5 μl) was further subjected to PCR under conditions similar to those described above, except that primers P3 and P4 were used.

The final product was cloned into a pET23b (product of Novagen Co., Ltd.), and the DNA-sequence thereof was confirmed by use of an ABI377DNA sequencer (product of PE-ABI Co., Ltd.).

The final product was treated with phenol/chloroform, and precipitated with ethanol, followed by dissolution in TE buffer. Both ends of the DNA were cut by use of restriction enzymes NdeI and XhoI.

The DNA fragment obtained by use of the restriction enzymes NdeI and XhoI was inserted into a pET23b vector through ligation.

The sequence of the thus-obtained gene was determined through sequencing and was found to be a novel sequence. The gene was named the "GFAT1L gene."

The full length of the coding region of the thus-obtained gene consists of 2097 bases represented by SEQ ID NO: 1. The amino acid sequence encoded by the base sequence consists of 699 amino acid residues represented by SEQ ID NO: 2. The gene is a human cDNA (full length: 2097 bases) coding for the amino acid sequence.

The GFAT1L gene of the present invention was confirmed to be a novel gene having such a sequence that 54 bases are inserted between the 684th and the 685th bases of the human GFAT gene, which was cloned by McKnight et al. (McKnight, G. L., et al., J. Biol. Chem., 267, 25208–25212 (1992)). The amino acid sequence of the protein encoded by the GFAT1L gene sequence was found to have a structure such that a sequence composed of 18 amino acid residues is inserted between the 228th and the 229th amino acid residues.

In the tests described hereinunder, the novel gene isolated by the present inventors is referred to as the "GFAT1L gene" and the human GFAT gene according to McKnight et al. is referred to as the "GFAT1S gene."

Example 2

Expression patterns of the GFAT1L gene in various organ tissues were studied by employment of RT-PCR, and the expression patterns of the GFAT1L gene were compared with those of the GFAT1S gene.

QUICK-Clone cDNAs (products of Clontech Co., Ltd.; heart, brain, liver, skeletal muscle, small intestine, kidney, pancreas, and fat) were employed as test samples.

Primers having sequences represented by SEQ ID NOs: 7 and 8 were synthesized and used. ExTaq (product of Takara Shuzo Co., Ltd.) was also used.

PCR was carried out firstly at 95° C. for one minute, and subsequently, 40 reaction cycles each consisting of 95° C. for 30 seconds, 55° C. for 30 seconds, and 72° C. for 45 seconds. A portion of the reaction product was electrophorased on 4% agarose gel, to thereby obtain the expression pattern of each gene.

The results are shown in FIG. 1.

Legends given for respective lanes in FIG. 1 and corresponding organ tissue (in parenthesis following its corresponding legend) are as follows:

Marker (marker), Heart (heart), Brain (brain), Liver (liver), Skeletal Muscle (skeletal muscle), Kidney (kidney), Pancreas (pancreas), Small Intestine (small intestine), and Fat (fat).

As shown in FIG. 1, the GFAT1L gene was confirmed to exhibit strong expression in the heart and skeletal muscle, and very weak expression in the brain. It was also confirmed that only GFAT1S gene exhibited expression in other organs subjected to the test.

Thus, expression of the gene of the present invention was found to be tissue-specifically controlled.

Example 3

Preparation of GFAT1L Recombinant Protein

A human GFAT1L gene or a GFAT1S gene (for comparison purpose) was inserted into a pET23b vector (product of Novagen Co., Ltd.), and BL21-CodonPlus(DE3)RIL (product of Stratagene Co., Ltd.) was subjected to transformation by use of the thus-obtained vector. The transformant was incubated overnight at 37° C. in ampicillin-containing LB medium. On the following day, a liquid culture (50 ml) was added to the ampicillin-containing LB medium (1 L), followed by incubation at 37° C. for an additional 90 minutes. 1M isopropylβ-D-(−)-thiogalactopyranosid (IPTG: product of Wako Pure Chemicals Industries, Ltd.: 2 ml) was added to the thus-obtained mixture, followed by incubation at 20° C. overnight, to thereby elicit expression of a recombinant protein.

The thus-obtained liquid culture was centrifuged at 7000 rpm for five minutes, to thereby collect E. coli cells, and the E. coli cells were washed once with Dulbecco's PBS(−) (product of Nihon Pharmaceutical Co., Ltd.; 50 ml) at 0° C. Subsequently, dithiothreitol (DTT: 5 mM) and sodium phosphate buffer containing 20% glycerol (pH=8.0; 50 mM) were suspended therein, to thereby yield a final volume of 40 ml, and the suspension was subjected to ultrasonic treatment, to thereby lyze the cells. The lyzate was ultracentrifuged at 30,000 rpm at 4° C. for 30 minutes, and insoluble matter was removed therefrom.

In the aforementioned manner, a supernatant containing a desired recombinant protein was obtained. The supernatant was divided into portions (1 ml each), quickly frozen by use of liquid nitrogen, and stored at −80° C. until use.

Example 4

Study on Difference in Characteristics between GFAT1L and GFAT1S

1. GFAT Activity Assay Method

GFAT activity was determined in accordance with Marshall et al. by means of spectrophotometry using a microplate (96 wells) (Journal of Biological Chemistry, vol. 266 No. 8, 4706–4712 (1991)) in the following manner. Glutamate produced by GFAT was allowed-to react with glutamate dehydrogenase (GDH), during which a reductive reaction of coenzyme APAD into APADH proceeded simultaneously. Changes in absorbance that accompany the reduction reaction of APAD to APADH are considered to represent GFAT activity.

Briefly, an appropriately diluted solution of a lyzate of GFAT1L- or GFAT1S-introduced E. coli (50 µl) was added to a substrate solution (200 µl) containing a sodium phosphate buffer (pH=7.5; 40 mM), potassium chloride (50 mM), EDTA (1.25 mM), APAD (0.3 mM), GDH (6 U/ml), glutamine (0–6 mM), and fructose-6-phosphate (F-6-P: 0–6 mM), and the mixture was allowed to react at 37° C. for 60 minutes. The absorbance change at 365 nm associated with the reaction was measured by use of a microplate reader.

2. Difference in Terms of Enzymatic Behavior between GFAT1L and GFAT1S

In order to study the difference in terms of enzymatic behavior between GFAT1L and GFAT1S, Km values were determined using, as substrates, glutamine and F-6-P. Km values were calculated on the basis of :S/v–S plotting and v–v/S plotting, which were made with regard to the enzyme substrate concentration (S) and activity of the enzyme (reaction rate (v)). Using the :S/v–S plotting, Km value was calculated from the point at which the X-axis and the line obtained from the plotting intersects (point of intersection corresponds to "−Km"), whereas using the v–v/S plotting, Km value was calculated from the slope of the line (the slope=−Km).

Since UDP-N-acetylglucosamine (UDP-GlcNAc) has been reported to inhibit GFAT activity (Journal of Biological Chemistry vol. 241, 1705–1712 (1966)), the inhibition pattern thereof was also examined. The inhibition pattern was determined from the appearance of the line obtained through plotting in a manner similar to that described above.

Figure 2:
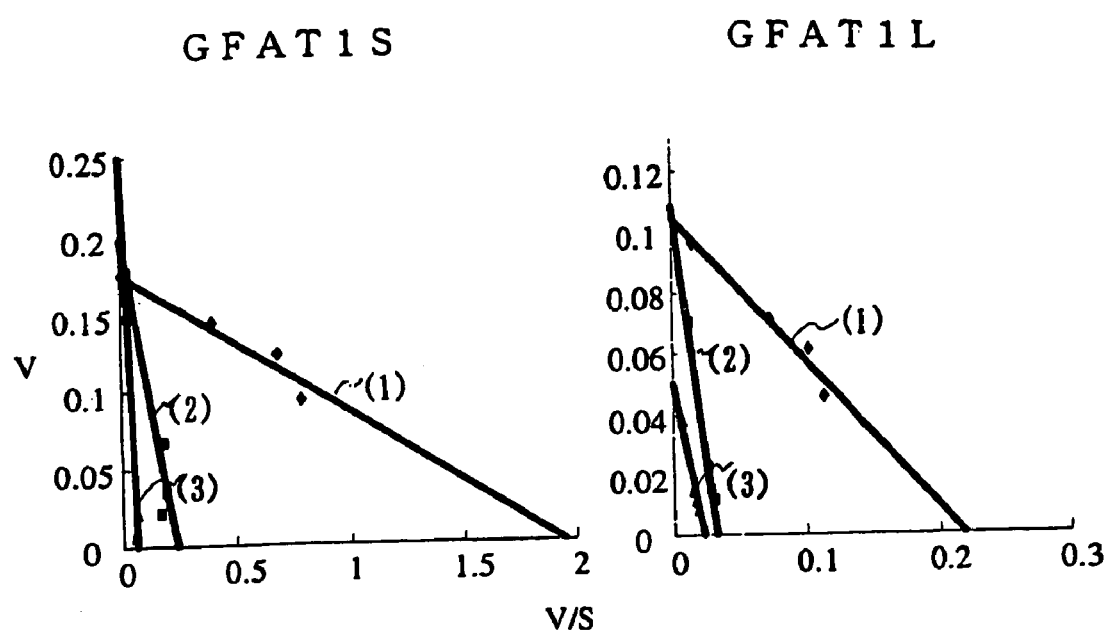
FIG. 2 is a graph for obtaining, according to Example 4, the Km value and the inhibitory pattern of GFAT activity, which are enzymatic characteristics of the GFAT1L of the present invention, when F-6-P is used as a substrate.
Figure 3:
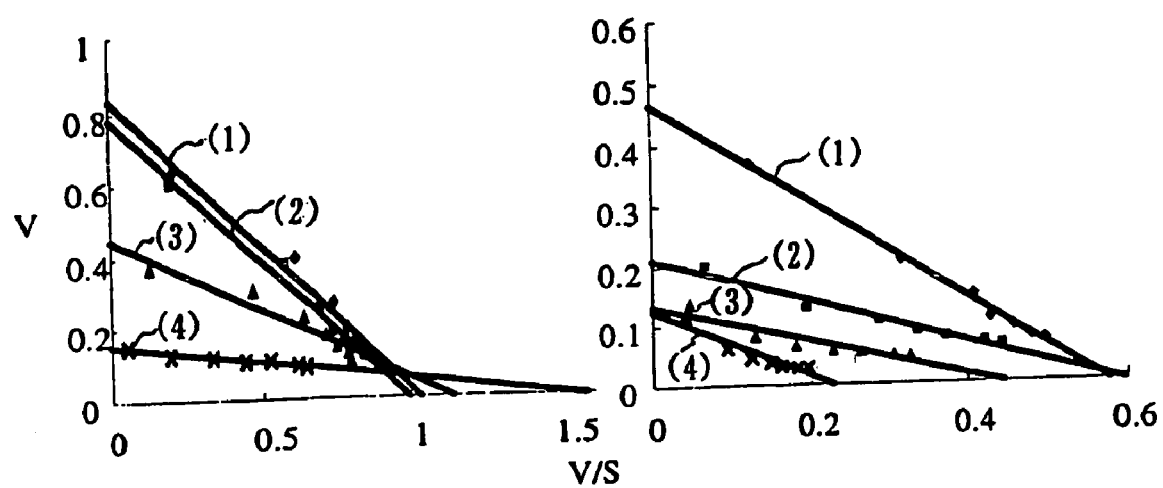
FIG. 3 is a graph for obtaining, according to Example 4, the Km value and the inhibitory pattern of GFAT activity, which are enzymatic characteristics of the GFAT1L of the present invention, when glutamine is used as a substrate.

The results are shown in FIGS. 2 and 3 and Table 1.

FIG. 2 shows graphs showing inhibition patterns of UDP-GlcNAc against GFAT activities of GFAT1S and GFAT1L in the case in which F-6-P was used as a substrate. The Y-axis corresponds to the reaction rate (v) of the enzyme, and the X-axis corresponds to (reaction rate (v))/(concentration of the enzyme substrate (s)).

In FIG. 2, the graph on the left shows the results concerning GFAT1S, and the graph on the right shows the results concerning GFAT1L. In the two graphs, lines (1) correspond to results through no UDP-GlcNAc addition, lines (2) correspond to results through UDP-GlcNAc addition (30 μM), and lines (3) correspond to results through UDP-GlcNAc addition (100 μM).

As shown in the graphs in FIG. 2, Km values were determined to be 90 μM for GFAT1S and 478 μM for GFAT1L, and inhibition patterns against GFAT activity were found to be "competitive inhibition" (in the case of GFAT1S) and "mixed inhibition" (in the case of GFAT1L), respectively.

FIG. 3 shows graphs showing inhibition patterns of UDP-GlucNAc against GFAT activity of GFAT1S and GFAT1L in the case in which glutamine was used as a substrate. The Y-axis represents the reaction rate (v) of the enzyme and the X-axis represents the ratio, (reaction rate (v))/(concentration of the enzyme substrate (s)).

In FIG. 3, the graph on the left shows the results concerning GFAT1S and the graph on the right shows the results concerning GFAT1L. In the graphs in FIG. 3, lines (1) correspond to the results obtained from no UDP-GlcNAc addition, lines (2) correspond to the results obtained from UDP-GlcNAc addition (10 μM), lines (3) correspond to the results obtained from UDP-GlcNAc addition (30 μM), and lines (4) correspond to the results obtained from UDP-GlcNAc addition (100 μM).

As shown in the graphs in FIG. 3, Km values were determined to be 822 μM for GFAT1S and 804 μM for GFAT1L, and inhibition patterns against GFAT activity were found to be "non-competitive inhibition" (in the case of GFAT1S) and "mixed inhibition" (in the case of GFAT1F), respectively.

TABLE 1

|  |  | GFAT1S | GFAT1L |
|---|---|---|---|
| Km value (μM) | F-6-P | 78–118 | 458–478 |
|  | Glutamine | 761–822 | 804–812 |
| Inhibition pattern | Glutamine | Un-competitive inhibition | Mixed inhibition |
|  | F-6-P | Competitive inhibition | Mixed inhibition |

FIGS. 2 and 3 and Table 1 have revealed that when F-6-P was used, there is a significant difference between Km values of GFAT1S (about 100 μM) and GFAT1L (about 500 μM); whereas when glutamine was used, there is no significant difference between Km values of GFAT1S (about 800 μM) and GFAT1L (about 800 μM)

UDP-GlcNAc exhibited the following inhibition patterns: when F-6-P was used as a substrate, GFAT1S was inhibited through competitive inhibition, and GFAT1L was inhibited through mixed inhibition in which competitive inhibition and non-competitive inhibition occur simultaneously; whereas when glutamine was used as a substrate, GFAT1S was inhibited through un-competitive inhibition, and GFAT1L was inhibited through mixed inhibition in which un-competitive inhibition and inhibition of another type occur simultaneously.

From the above results, the following differences were confirmed in terms of enzymatic behavior between GFAT1L according to the present invention and human GFAT. (1) Km values of GFAT1L of the present invention with respect to F-6-P are about five times as high as those of human GFAT1; (2) UDP-GlcNAc inhibits in a different pattern.

3. Study on Effects of GFAT1L on Insulin Resistance

GFAT has already been reported to affect insulin resistance in in vitro and in vivo tests. However, the discovery of the novel gene by the present inventors has revealed the existence of two subtypes of GFAT; i.e., GFAT1L and human GFAT (GFAT1S). The extent to which insulin resistance is affected by GFAT1L or human GFAT (GFAT1S) will be discussed hereinbelow.

Generally, healthy subjects metabolize about 70% blood glucose in skeletal muscle through insulin stimulation. In contrast, it has been reported that glucose availability in skeletal muscle of type II diabetic patients is as low as 30% and that glucose availabilities in other organ tissues are almost as same as those of healthy subjects (Journal of Clinical Investigation, 76 (1), 149–155 (1985)). Thus, skeletal muscle is considered to predominantly exhibit insulin resistance. It has been found that GFAT1L of the present invention is expressed in skeletal muscle, whereas GFAT1S is not expressed in the same. Therefore, GFAT1L of the present invention is considered to affect insulin resistance predominantly.

From the study on enzymatic behavior of GFAT1S and GFAT1L showing that (1) Km value of GFAT1L of the present invention with respect to F-6-P is about five times as high as that of GFAT1S and that (2) Since the intracellular glutamine concentration is 4–5 mM, GFAT activity depends on intracellular F-6-P concentration, in conjunction with a previous report that (3) the F-6-P concentration in erythrocytes of a type II diabetic patient is several tens of μM (Horm. Metabol. Res., 14, 233–236 (1982)), the following are speculated.

Figure 4:
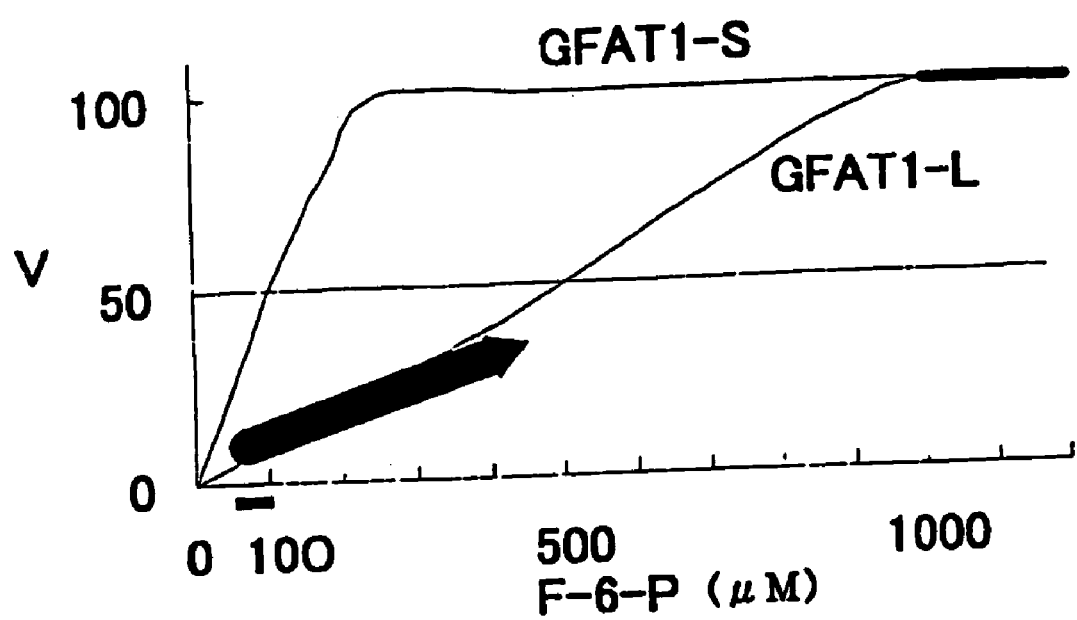
FIG. 4 is a graph showing an enzymatic reaction curve of the GFAT1L (activation state of GFAT) according to Example 4.

Briefly, as is apparent from FIG. 4, regarding GFAT activity speculated from the F-6-P concentration reported in that publication, GFAT1S acts steadily at a concentration close to the Km value and GFAT1L is hardly activated.

FIG. 4 is a graph of enzyme reaction curves of GFAT1S and GFAT1L (activation state of GFAT). The Y-axis represents reaction rate of the enzyme (v), and the X-axis represents intracellular F-6-P concentration (μEM). The higher the concentration, the higher the amount of glucose that flowed into cells. In FIG. 4, the bold line represents the F-6-P concentration in erythrocytes of non-insulin-dependent diabetics reported in literature, and the bold arrow indicates contribution to insulin resistance.

Moreover, the following is noted. Upon stimulation with insulin, intake of glucose into cells is multiplied. In this case, for GFAT1S, since enzymatic reaction reaches Vmax, when glucose is further flown into cells, GFAT activity is saturated and no further activation will occur. In contrast, for GFAT1L of the present invention, as the amount of glucose that flows into cells increases, GFAT is activated and the amount of metabolites increases accordingly, thereby inhibiting transfer of glucose transporters into cells through the cell membrane, leading to elevation of blood sugar (provided that Vmax of GFAT1L and that of GFAT1S are almost the same).

Accordingly, as compared with GFAT1S, GFAT1L of the present invention is considered to closely participate in insulin resistance. Thus, GFAT1L of the present invention is concluded to play an important role in the mechanism of insulin resistance.

INDUSTRIAL APPLICABILITY

The present invention provides a GFAT1L gene encoding a novel human protein homologue having a homology to human GFAT.

The gene of the present invention is highly expressed in skeletal muscle and the heart, which are important tissues for glycometabolism, and the gene is considered to promote GFAT activity in such tissues and peripheral tissues, or the hexosamine biosynthesis pathway in the glycolysis system. In addition, the gene is considered to prevent glucose transporters from transferring to cell membranes. Therefore, since the gene effectively acts on regulation of the blood glucose level in glycometabolism, analysis of the degree of expression or the GFAT activity of the gene is utilized for studies on the relation between the function of genes related to the gene and glycometabolism-related diseases. Particularly, the gene can be used for gene diagnosis of patients with hypoglycemia or diabetes, and used for research on pharmaceutical application of an antibody against an expression product of the gene or antisense DNA of the product.

By utilizing the gene of the present invention, expression of the gene in a variety of tissues can be investigated, and the function of the gene in a living organism can be analyzed.

By using the gene, a GFAT1L protein encoded by the gene can be mass-produced by means of a gene engineering technique. Provision of the protein enables investigation of GFAT1L activity and binding activity of the GFAT1L protein.

The protein of the present invention is useful for elucidation, diagnosis, and treatment of diseases related to the GFAT1L gene and the expression product thereof (for example, diseases related to GFAT activity or regulation of the hexosamine biosynthesis pathway in the glycolysis system; diseases related to hypoglycemia and blood glucose level regulation; hypoglycemia; diabetes; and diabetic complications such as diabetic nephropathy, diabetic retinopathy, and diabetic neuropathy).

The present invention also provides a gene introduction vector containing an antisense oligonucleotide of the gene of the present invention, the vector being useful for gene therapy; a gene therapeutic agent containing, as active ingredients, a cell into which the antisense oligonucleotide of the GFAT1L gene and the vector or the cell; and a gene therapy method employing the therapeutic agent.

The present invention also provides a drug containing, as an active ingredient, the antisense oligonucleotide of the gene of the present invention, an antibody which can be bound to GFAT1L, or a fragment of the antibody, which drug prevents expression of GFATmRNA in skeletal muscle, particularly in smooth cells of skeletal muscle, and thus can be used for treating diseases and pathological conditions such as diabetes and diabetic complications.

The present invention also provides a method and a kit for screening a candidate compound which inhibits the enzyme activity of the GFAT1L protein and the expression product of the GFAT1L gene, and is used for treating diabetes.

The invention claimed is:

1. An isolated polynucleotide encoding a polypeptide comprising:
   the amino acid sequence of SEQ ID NO: 2,
   or the complementary strand of said isolated polynucleotide.

2. The isolated polynucleotide of claim 1 which comprises the polynucleotide sequence of SEQ ID NO: 1, or the full complement of SEQ ID NO: 1.

3. A recombinant expression vector comprising the polynucleotide of claim 1 or 2.

4. An isolated host cell comprising the recombinant expression vector of claim 3.

5. An expression product of the polynucleotide of claim 1 or 2.

6. An isolated polypeptide comprising:
   the amino acid sequence of SEQ ID NO: 2.

7. A composition comprising, as an active ingredient, the expression product of claim 5.

8. A composition comprising, as an active ingredient, the polypeptide of claim 6.

* * * * *

SEQUENCE LISTING

<160> NUMBER OF SEQ ID NOS: 7

<210> SEQ ID NO 1
<211> LENGTH: 2097
<212> TYPE: DNA
<213> ORGANISM: Homo sapiens

<400> SEQUENCE: 1

```
atgtgtggta tatttgctta cttaaactac catgttcctc gaacgagacg agaaatcctg      60
gagaccctaa tcaaaggcct tcagagactg gagtacagag gatatgattc tgctggtgtg     120
ggatttgatg gaggcaatga taaagattgg gaagccaatg cctgcaaaat ccagcttatt     180
aagaagaaag gaaaagttaa ggcactggat gaagaagttc acaagcaaca agatatggat     240
ttggatatag aatttgatgt acaccttgga atagctcata cccgttgggc aacacatgga     300
gaacccagtc ctgtcaatag ccaccccag cgctctgata aaaataatga atttatcgtt      360
attcacaatg gaatcatcac caactacaaa gacttgaaaa agttttttgga aagcaaaggc     420 tatgacttcg aatctgaaac agacacagag acaattgcca agctcgttaa gtatatgtat     480
gacaatcggg aaagtcaaga taccagcttt actaccttgg tggagagagt tatccaacaa     540
ttggaaggtg ctttttgcact tgtgtttaaa agtgttcatt ttcccgggca agcagttggc     600
acaaggcgag gtagccctct gttgattggt gtacggagtg aacataaact ttctactgat     660
cacattccta tactctacag aacagctagg actcagattg gatcaaaatt cacacggtgg     720
ggatcacagg gagaaagagg caaagacaag aaaggaagct gcaatctctc tcgtgtggac     780
agcacaacct gccttttccc ggtggaagaa aaagcagtgg agtattactt tgcttctgat     840
gcaagtgctg tcatagaaca caccaatcgc gtcatctttc tggaagatga tgatgttgca     900
```

-continued

```
gcagtagtgg atggacgtct ttctatccat cgaattaaac gaactgcagg agatcacccc      960
ggacgagctg tgcaaacact ccagatggaa ctccagcaga tcatgaaggg caacttcagt     1020
tcatttatgc agaaggaaat atttgagcag ccagagtctg tcgtgaacac aatgagagga     1080
agagtcaact ttgatgacta tactgtgaat ttgggtggtt tgaaggatca cataaaggag     1140
atccagagat gccggcgttt gattcttatt gcttgtggaa caagttacca tgctggtgta     1200
gcaacacgtc aagttcttga ggagctgact gagttgcctg tgatggtgga actagcaagt     1260
gacttcctgg acagaaacac accagtcttt cgagatgatg tttgcttttt ccttagtcaa     1320
tcaggtgaga cagcagatac tttgatgggt cttcgttact gtaaggagag aggagcttta     1380
actgtgggga tcacaaacac agttggcagt tccatatcac gggagacaga ttgtggagtt     1440
catattaatg ctggtcctga gattggtgtg ccagtacaa aggcttatac cagccagttt       1500
gtatcccttg tgatgtttgc ccttatgatg tgtgatgatc ggatctccat gcaagaaaga     1560
cgcaaagaga tcatgcttgg attgaaacgg ctgcctgatt tgattaagga agtactgagc     1620
atggatgacg aaattcagaa actagcaaca gaactttatc atcagaagtc agttctgata     1680
atgggacgag gctatcatta tgctacttgt cttgaagggg cactgaaaat caaagaaatt     1740
acttatatgc actctgaagg catccttgct ggtgaattga acatggccc tctggctttg       1800 gtggataaat tgatgcctgt gatcatgatc atcatgagag atcacactta tgccaagtgt     1860
cagaatgctc ttcagcaagt ggttgctcgg caggggcggc ctgtggtaat ttgtgataag     1920
gaggatactg agaccattaa gaacacaaaa agaacgatca aggtgcccca ctcagtggac     1980
tgcttgcagg gcattctcag cgtgatccct ttacagttgc tggctttcca ccttgctgtg     2040
ctgagaggct atgatgttga tttcccacgg aatcttgcca aatctgtgac tgtagag       2097
```

<210> SEQ ID NO 2
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 2

```
gttccgcgta ctcgtcgtga aatcctggag acc                                    33
```

<210> SEQ ID NO 3
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 3

```
gcttacctga actaccacgt tccgcgtact cgt                                    33
```

<210> SEQ ID NO 4
<211> LENGTH: 40
<212> TYPE: DNA
<213> ORGANISM: ARTIFICIAL SEQUENCE
<220> FEATURE:
<223> OTHER INFORMATION: SYNTHETIC DNA

<400> SEQUENCE: 4

```
ttttttttcat atgtgtggta tctttgctta cctgaactac                            40
```

```
<210> SEQ ID NO 5
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ccctcgagtt actctacagt cacagatttg gc                          32

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
agccctctgt tgattggtgt                                        20

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
tccatctgga gtgtttgcac                                        20
```